United States Patent [19]
Klein et al.

[11] Patent Number: 5,963,456
[45] Date of Patent: Oct. 5, 1999

[54] METHOD AND APPARATUS FOR DISPLAYING CAPILLARY ELECTROPHORESIS DATA

[75] Inventors: Gerald L. Klein, Orange; Steven P. Katzmann, Yorba Linda, both of Calif.

[73] Assignee: Beckman Instruments, Inc., Fullerton, Calif.

[21] Appl. No.: 08/757,498

[22] Filed: Nov. 27, 1996

Related U.S. Application Data

[63] Continuation of application No. 08/486,528, Jun. 7, 1995, abandoned, which is a continuation of application No. 07/916,307, Jul. 17, 1992, abandoned.

[51] Int. Cl.$^6$ .................................................. G06F 159/00
[52] U.S. Cl. .................... 364/496; 345/131; 356/344; 430/32; 430/34; 430/38; 204/451; 204/455; 204/456; 204/600; 204/601; 204/603; 204/604; 204/606
[58] Field of Search .................................. 364/496, 497, 364/498, 526, FOR 117, FOR 114, FOR 115; 356/394; 395/202, 203; 345/107, 88, 89, 90, 131; 430/32, 34, 38; 204/451, 455, 456, 600, 601, 603, 604, 606

[56] References Cited

U.S. PATENT DOCUMENTS

| | | | |
|---|---|---|---|
| 3,932,264 | 1/1976 | Haruki et al. | 204/299 |
| 3,956,099 | 5/1976 | Israel et al. | 204/299 R |
| 4,061,561 | 12/1977 | Fletcher et al. | 204/616 |
| 4,124,470 | 11/1978 | Dahms | 204/180 R |
| 4,130,471 | 12/1978 | Grunbaum | 204/182.8 |
| 4,154,669 | 5/1979 | Goetz | 204/299 R |
| 4,298,570 | 11/1981 | Liggig et al. | 422/64 |
| 4,343,991 | 8/1982 | Fujiwara et al. | 250/227.11 |
| 4,375,401 | 3/1983 | Catsimpoolsas | 204/301 |
| 4,439,680 | 3/1984 | Broadhurst | 250/310 |
| 4,592,089 | 5/1986 | Hartman | 382/6 |
| 4,706,192 | 11/1987 | Nasu et al. | 364/413.01 |

(List continued on next page.)

FOREIGN PATENT DOCUMENTS

| | | |
|---|---|---|
| 0 339 779 | 11/1989 | European Pat. Off. |
| 0371573 | 6/1990 | European Pat. Off. |
| 0488422 | 6/1992 | European Pat. Off. |
| 4012685 | 10/1990 | Germany . |

OTHER PUBLICATIONS

"Evaluation of an Automatic Siphonic Sampler for Capillary Zone Electrophoresis", by Honda, Iwase and Fujiwara, *Journal of Chromatography*, vol. 404 (1987) pp. 313–320.
"Capillary Zone Electrophoresis", by Jorgenson and Lukacs, *Science*, vol. 222, pp. 266–272.
"Characterization and Automation of Sample Introduction Methods for Capillary Zone Electro–phoresis," by Rose and Jorgenson, *Anal. Chem.* 1988, vol. 60, No. 7, pp. 642–648.
"Quantitation of Picogram Quantities of Serum Albumin by Ultramicrodisc Electrophoresis and Direct Densitometry," by Oken, *Microchemical Journal*, vol. 15, (1970), pp. 557–563.
Dorland's Pocket Medical Dictionary, Published 1989 by W.B. Saunders Co, : p. 200.
Foley and Van Dam: Fundamentals of Interactive Computer Graphics, Published 1982 by Addison–Wesley Pub. Co., pp. 132–133 & 611–619.
Huang, X.C. et al., "Capillary Array Electrophoresis Using Laser–Excited Confocal Fluorescence Detection," *Analytical Chemistry* 64(8):967–972 (Apr. 15, 1992).

*Primary Examiner*—Robert A. Weinhardt
*Assistant Examiner*—Joseph Thomas
*Attorney, Agent, or Firm*—William H. May; Gary T. Hampson; Sheldon & Mak

[57] ABSTRACT

A method and apparatus for displaying capillary electrophoresis data wherein absorbance with respect to time is related to graphic values within a graphic range or scale of values and selected graphic values are displayed with respect to time. The selected graphic values may comprise a range hues, color saturation and/or brightness or may represent a monochromatic scale. The resulting representation may be horizontally aligned with the corresponding electrophoretogram absorbance values to provide both a quantitative value (electrophoretogram absorbance values) and qualitative (graphic stripe) display.

73 Claims, 12 Drawing Sheets

U.S. PATENT DOCUMENTS

| | | | |
|---|---|---|---|
| 4,816,123 | 3/1989 | Ogan et al. | 204/183.3 |
| 4,857,731 | 8/1989 | Tagata | 250/310 |
| 4,865,090 | 9/1989 | Burolla et al. | 141/165 |
| 4,906,344 | 3/1990 | Hjerten | 264/182.8 |
| 4,911,807 | 3/1990 | Burd | 204/180.1 |
| 4,927,265 | 5/1990 | Brownlee | 356/73 |
| 4,985,129 | 1/1991 | Burd | 204/299 R |
| 4,999,300 | 3/1991 | Barton | 435/252.34 |
| 5,019,236 | 5/1991 | Young | 204/299 R |
| 5,031,157 | 7/1991 | Anderson et al. | 367/110 |
| 5,045,172 | 9/1991 | Guzman | 204/299 R |
| 5,061,361 | 10/1991 | Gordon | 204/299 R |
| 5,066,382 | 11/1991 | Weinberger et al. | 204/299 R |
| 5,085,757 | 2/1992 | Karger et al. | 204/299 R |
| 5,092,972 | 3/1992 | Ghowsi | 204/454 |
| 5,141,612 | 8/1992 | Schomburg et al. | 204/455 |
| 5,145,567 | 9/1992 | Hsieh et al. | 204/180.1 |
| 5,194,949 | 3/1993 | Poulsen et al. | 348/138 |
| 5,246,577 | 9/1993 | Fuchs et al. | 210/198.2 |
| 5,264,095 | 11/1993 | Hsieh et al. | 204/180.1 |
| 5,273,633 | 12/1993 | Wang | 204/180.1 |
| 5,413,686 | 5/1995 | Klein et al. | 204/299 R |

METHOD AND APPARATUS FOR DISPLAYING CAPILLARY ELECTROPHORESIS DATA

This is a continuation of application Ser. No. 08/486,528 filed on Jun. 7, 1995 abandoned, which is a continuation of application Ser. No. 07/916,307 filed on Jul. 17, 1992 abandoned.

FIELD

The present invention relates generally to the field of electrophoresis and more particularly to capillary electrophoresis, and still more particularly to a method and apparatus for displaying capillary electrophoresis data. The invention may be used in, but is not necessarily limited to, clinical chemistry.

BACKGROUND

The value of electrophoresis in clinical chemistry has been recognized for some time in the analysis, for example, of proteins in serum as well as other body fluids. The use of electrophoresis in the clinical laboratory began in the early 1950s with the electrophoresis performed on paper strips. Proteins in, for example, serum were separated along a buffer-wetted strip of paper. After the separation was complete, the separated proteins were fixed and stained to produce visible patterns. These patterns were in the form of visible bands perpendicular to the direction of protein flow under the influence of the electrophoresizing voltage. In the interpretation of these electrophoresis patterns or bands, the relative intensities of the stained bands were examined to identify the proteins and the relative concentrations of the proteins within the sample.

The paper strips were later replaced with microporous membranes of either cellulose acetate or cellulose nitrate which provided better resolution due to the smaller pore size of these support materials. In addition to fixing and staining these membranes, the membranes could be "cleared" by soaking the membranes in a solvent, thereby collapsing the membrane pores without effecting the relative position of the stained bands.

With a microporous membrane thusly cleared, the membrane could be scanned by a scanning densitometer for quantitation of the visible protein bands. Such a scanning densitometer would use an illuminated slit and an optical detector on opposite sides of the membrane, generating a detected signal proprotional to the relative density of the protein bands. The resulting detected signal was displayed as a graph with density along the vertical axis and the relative gel position along the horizontal axis. The result was a representation of stain density and thus protein density along the membrane, with peaks along the graph corresponding to respective density maxima along the membrane. By comparing the areas under the peaks corresponding to the protein bands, a quantitative assessment of the relative distribution of the protein fractions contained in a sample could thus be made.

A next step in the development of clinical electrophoresis was the introduction of gel layers as the support media. A small quantity of the sample would be applied near one edge of a thin gel layer cast onto a stable backing material such as mylar. The gel would then be electrophoresized in a suitable electric field, processed by fixing and staining the separated protein fractions, and then viewed by examing the resulting stained gel directly or obtaining a quantitative scan of the gel in a scanning densitometer.

The interpretation of present clinical chemistry electrophoresis gels relies upon both the qualitative examination of the stained protein bands on the gel as well as the quantitative data of proportional protein content within the fractions indicated by the bands on the gel. Further, the gels may be incorporated as a part of a permanent medical record for later review, analysis or research. The gel patterns have thus become an important part of the pathologist's assessment of a patient's overall clinical condition in general and specific diagnostic interpretations in some instances.

Despite the success and acceptance of gel clinical electrophoresis, the technique requires skilled technicians and is time consuming, effectively limiting the number of tests that can be performed using the technique. Although automated gel electrophoresis analyzers are available, these analyzers are often very bulky and expensive, requiring considerable set-up time and effort.

Capillary electrophoresis is a more recent development and can be used to perform the type of electrophoretic separations presently performed with gels. In capillary electrophoresis, a small tube or capillary having an inside bore diameter in the range of about five microns to about two hundred microns and often about twenty cm long is filled with an electrically conductive fluid, or buffer. A small quantity of a sample to be analyzed is introduced into one end of the capillary bore and the ends of the capillary are placed into separate reservoirs of buffer. A direct current voltage in a range of about 2,000 volts to about 30,000 volts is applied to the ends of the capillary by means of electrodes positioned in the buffer reservoirs, causing a small current, typically in the range of about five microamps to about one milliamp, to flow through the capillary.

With the correct polarity applied across the capillary, the sample begins to migrate from the sample introduction end toward the other end of the capillary. As this migration occurs, different molecules in the sample travel at different rates primarily because of slightly different electrical charges on the molecules. These different migration rates cause molecules with slightly different charges to separate one from the other, some moving more quickly and advancing relatively with respect to more slowly moving molecules. As the sample nears the other end of the capillary, the small volume of sample becomes separated into bands of different molecules according to the relative migration rates of the molecules. These bands or groups of different molecules are detected near the other end of the capillary by, for example, passing a light beam through the bore of the capillary. Changes to the light beam, such as absorbance caused by the different molecules, are detected as the separated molecules pass through the beam, thus identifying the different molecules or the classes or categories of molecules in the sample and the relative concentration of such molecules.

Although automated forms of capillary electrophoresis analyzers are known in the art, none of such prior automated analyzers are suitable for routine clinical laboratory applications. The prior art analyzers require considerable manual manipulation despite their automated nature, allow only one sample to be electrophoresized at a time, have difficult capillary replacement procedures, or require additional external equipment such as high-pressure nitrogen tanks. In addition to these disadvantages, prior art capillary electrophoresis analyzers do not display the resulting electrophoretogram in a form that is readily acceptable to pathologists practicing in clinical chemistry laboratories. The failure of such prior analyzers to provide a display form or format that is usable by pathologists to evaluate the patient samples in a fashion consistent with gel electrophoresis represents a substantial and important drawback and disadvantage in such prior art systems with respect to the field of clinical chemistry.

Thus, there is a need for an automated capillary electrophoresis analyzer that provides a display form or format that is immediately and readily usable by pathologists in a fashion comparable to that obtained with gel electrophoresis. Further, there is a need for such an automated capillary electrophoresis analyzer that is easy to use, requires less sample manipulation, and is capable of substantially increased throughput as compared to prior capillary electrophoresis analyzers.

SUMMARY OF THE INVENTION

The present invention is directed to a display method and an apparatus for performing such a display method for use in a clinical chemistry capillary electrophoresis analyzer. The method and apparatus of the present invention generates a graphic representation or display that, in addition to, in place of, or along with an electrophoretogram representing absorbance with respect to electrophoresizing time, relates absorbance to graphic values within a graphic scale or range of values and which displays those graphic values. The visible graphic values may comprise a range of hues, color saturation and/or brightness (intensity) or may represent a monochromatic scale. The graphic values may be displayed in a stripe having a length related to the electrophoresizing time and a graphic value, such as intensity, within the stripe correlated to corresponding absorbance. The resulting stripe provides interpretive continuity between the known clinical gel electrophoresis art and the clinical capillary electrophoresis analyzer of the present invention.

A method according to the present invention may include electrophoresising a fluid in a capillary and detected a plurality of values related to the absorbance of the fluid in the capillary. The detected values are related to a range of graphic values. A graphic value is selected and displayed.

The step of relating the absorbance to a range of graphic values may include relating the absorbance to a range of absorbance values, determining a ratio according to the value of the absorbance within the range of absorbance values, and selecting the graphic value according to the ratio. The range of absorbance values may have upper and lower limits, and the upper limit may be variable. Alternatively, the upper and lower limits may be selected from the absorbance data to auto-scale the display according to the present invention.

An apparatus according to the present invention may include means for electrophoresising a fluid in a capillary and means for detecting a plurality of values related to the absorbance of the fluid in the capillary. The apparatus includes means for relating the detected values to a range of graphic values and selecting and displaying a graphic value.

The means for relating the absorbance to a range of graphic values may include means for relating the absorbance to a range of absorbance values, determining a ratio according to the value of the absorbance within the range of absorbance values, and selecting the graphic value according to the ratio. The range of absorbance values may have upper and lower limits, and the upper limit may be variable. Alternatively, the upper and lower limits may be selected from the absorbance data to auto-scale the display according to the present invention.

The present invention may also be used to display the results of other measurement techniques in capillary electrophoresis, such as data from fluorescence, radioactivity, and conductance measurements.

BRIEF DESCRIPTION OF THE DRAWINGS

These and other features, aspects, and advantages of the present invention will become better understood with reference to the following description, appended claims, and accompanying drawings where:

FIG. 14, comprising

DETAILED DESCRIPTION

Figure 1:
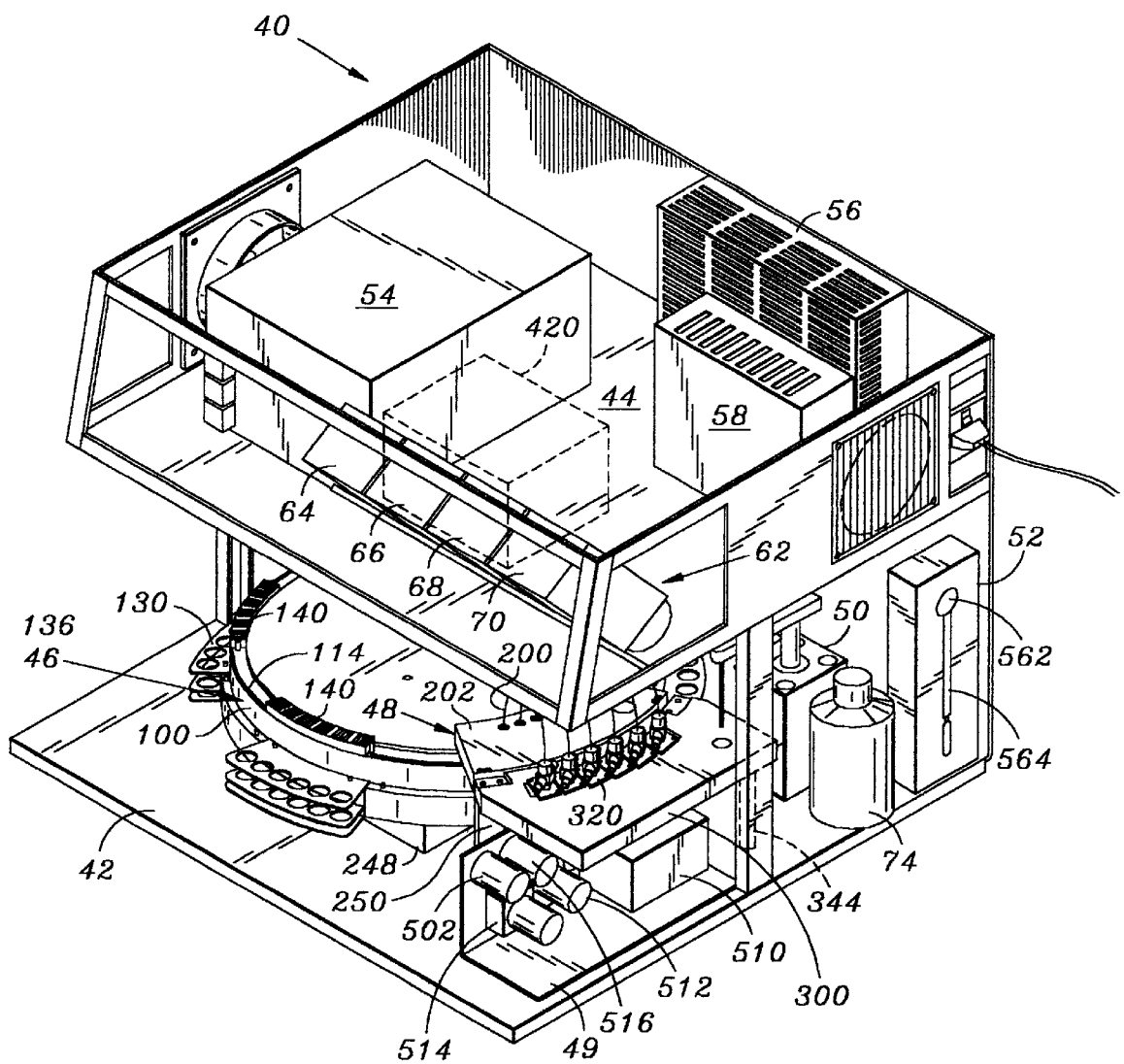
FIG. 1 is a perspective view of an analyzer in accordance with the present invention.
Figure 2:
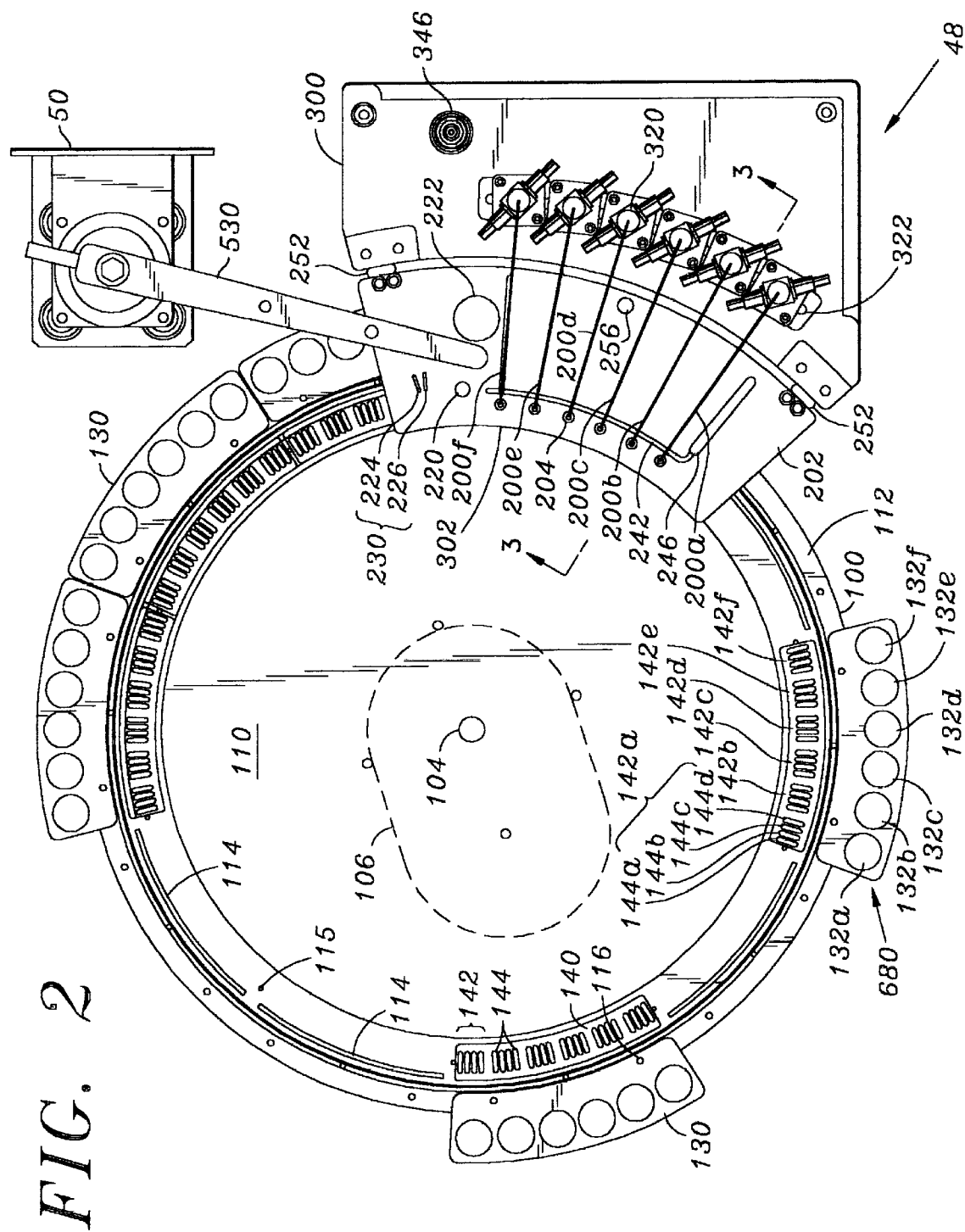
FIG. 2 is a top view of the turntable, capillary sample end platform and capillary detection end platform of the analyzer of FIG. 1.

With respect to FIGS. 1 and 2, an analyzer 40 in accordance with the present invention is formed on a chassis having a lower horizontal mounting plate 42 and an upper horizontal mounting tray 44. The mounting plate 42 supports a turntable assembly 46, a capillary assembly 48, a fluid control assembly 49, a probe assembly 50, and a pipettor-dilutor assembly 52. The upper mounting tray 44 supports a card cage 54, low voltage DC power supply 56, and light source power supply 58. A plurality of reagent reservoirs 62 are also supported at the front edge of the upper tray for easy access by an operator. Preferably, the reservoirs 62 include a water bottle 64, a buffer bottle 66 containing a suitable running buffer such as boric acid at pH 10.2, a wash solution bottle 68 containing sodium hydroxide (NaOH), and a diluent bottle 70 containing a suitable diluent such as phosphate buffered saline. The diluent may additionally include if desired specific chemical reference markers, such as is disclosed in U.S. patent application Ser. No. 708,424, filed May 31, 1991 in the name of Fu-Tai A. Chen, and entitled Identification of Sample Constituents Utilizing Capillary Electrophoresis. The placement of the reservoirs 62 on the upper tray 44 allows gravity feed of the reagents contained in the reservoirs 62 throughout the analyzer 40. The analyzer 40 may also include suitable top, side and front panels and doors (not shown in FIG. 1) to enclose the analyzer 40, all in a conventional fashion.

The turntable assembly 46 provides support and automated positioning for sample tubes and reagent segments. More particularly, the turntable assembly 46 includes a turntable 100 rotatably supported by a shaft 104 at the center of the turntable 100. The shaft 104 is part of a motor and drive belt assembly 106 (shown in simplified phantom outline in FIG. 2) that is supported by the mounting plate 42 and is beneath and inside the turntable 100. The motor and drive belt assembly 106 is operated so as to rotate the turntable 100 and shaft 104 in a controllable fashion.

The turntable 100 includes an upper surface 110 and a lower annular support 112. The upper surface 110 includes a plurality of arcuate ribs 114 disposed near the outer periphery of the upper surface 110 and, in the embodiment disclosed herein, the ribs 114 define ten equally spaced positions about the periphery of the upper surface 110. Between the ribs 114 are pins 115. The lower annular support 112 includes posts 116 extending upwardly from the surface 112. Pairs of posts 116 are disposed radially outwardly with respect to each of the ribs 114. Thus, twenty posts 116 are disposed on the annular support 112 with respect to the ten corresponding ribs 114.

The turntable 100 also includes an inner depending lip 118 (FIG. 3) that includes ten equally spaced notches (not shown) formed into the lower edge of the lip 118. The notches are sized to be detected by an optical detector (not shown) to thus determine the rotational position of the table 100, all in a conventional fashion.

Sample tube sectors 130 may be suspended from the annular support 112 and posts 116 to support a plurality of sample tubes, such as blood draw or sample tubes 132, about the periphery of the turntable 100. The sample tube sectors 130 include a horizontal flange 134 that is adapted to rest upon the annular support 112 and two holes 136 that receive the posts 116 to thereby removably secure the sample sector 130 to the turntable 100, the horizontal flange 134 resting upon the annular support 112.

A plurality of reagent segments 140 may be removably positioned about the periphery of the upper surface 110. Each reagent segment 140 is curved to match the curve at the periphery of the upper surface 110. The reagent segments fit over the ribs 114, the ribs 114 thus fitting inside the reagent segments 140 near the outer edges thereof, thereby removably retaining the reagent segments 140 on the upper surface 110. The reagent segment 140 includes six reservoir groups 142 and each reservoir group 142 in turn includes four individual reservoirs 144. Each reservoir 144 is adapted to hold approximately 200 μl of liquid when filled to the maximum usable capacity. Five reagent segments 140 are seen in FIG. 2.

The capillary assembly 48 provides support for a plurality of capillaries as well as the associated electrodes for establishing current flow through the capillaries and optical fiber holders for positioning optical fibers used for detection. As used herein, the "sample end" of a capillary is the end into which a sample is introduced into the capillary before electrophoretic separation along the length of the capillary, and the "detection end" of a capillary is the end proximate the detection or detector means used to detect the results of electrophoretic separation occurring along the length of the capillary.

In the embodiment disclosed herein, the capillary assembly 48 supports six capillaries 200, also sometimes identified individually in this specification and in the figures as capillaries 200a–200f as appropriate. The capillaries 200 are conventional silica quartz glass capillaries formed with a thin conformal coating of a polyimide, having an inside diameter within a range of about five microns to two hundred microns and more particularly in a range of approximately twenty five microns to seventy five microns, and an outer diameter of about one hundred forty microns to three hundred seventy five microns, respectively.

Figure 4:
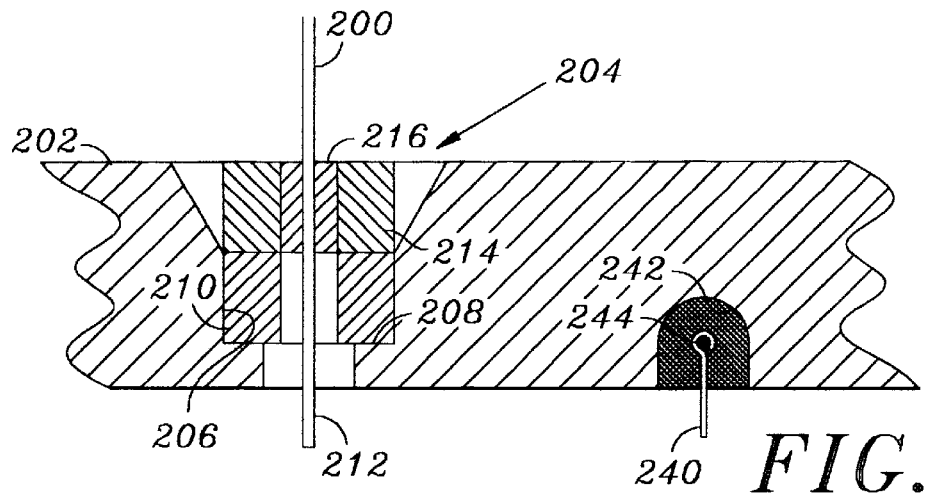
FIG. 4 is an enlarged side section view of the sample end of the capillaries.

The sample ends of the capillaries 200 are removably supported by a sample end plate 202. The sample end plate 202 is generally arcuate and includes six capillary end retainers 204 (FIG. 4). The vertical center lines of the capillary end retainers 204 are spaced to align with the spacing between corresponding ones of the reservoirs 144 within the reservoir groups 142 of a reagent segment 140 positioned on the turntable 100. This spacing aligns the ends of the capillaries 200 over, for example, a first one of the reservoirs 144 within each reservoir group 142 when so positioned by the rotation of the turntable, and so on.

Each of the retainers 204 includes a shouldered hole 206 through the sample end plate 202 defining an annular shoulder 208. A polarized barium ferrite annular magnetic 210 is fixed within the hole 206 against the shoulder 208.

To be retained by the sample end plate 202, sample end 212 of each of the capillaries 200 includes a second polarized barium ferrite annular magnets 214 bonded to the capillary 200 proximate the sample end 202 by means of a suitable rubber adhesive 216. With the capillary 200 positioned as illustrated in FIG. 4, the abutting ends of the magnets 210 and 214 are reverse polarized respectively, creating an attractive magnetic force between the magnets 214 and 210. The magnetic force thereby removably retains the capillary 200 within the sample end plate 202 and positions the sample end 212 for access to reservoirs 144 within a reagent segment 140 that may be carried by the turntable 100.

Two access holes 220 and 222 are formed through the sample end plate 202, the access hole 222 having a larger diameter than the access hole 220. The access hole 220 is formed to align over reservoirs 144 in reagent segments 140 that may be positioned on the turntable 100 beneath the sample end plate 202. The access hole 222 is aligned to provide access through the sample end plate 202 to sample tubes 132 that are held by the sample tube sectors 130 beneath the sample end plate 202.

Figure 5:
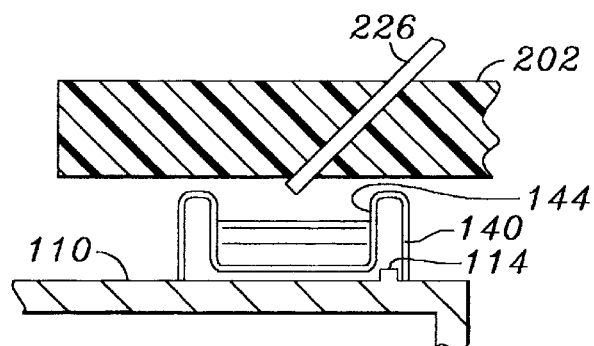
FIG. 5 is a side section view of a reagent delivery tube positioned to delivery reagent to a reagent segment.

Two lengths of small bore rigid tubing 224 and 226 are retained by the sample end plate 202 proximate the smaller access hole 220. Tubing lengths 224 and 226, forming a group 230 of reagent dispensing tubes, are of sufficient length to pass through the sample end plate 202 (FIG. 5) and are fixed at a slight angle with respect to vertical. The group 230 of tubes is positioned to deliver liquid reagents to reservoirs 144 of reagent segments 140 that may be positioned beneath the open ends of the tubing lengths 224 and 226 under the sample end plate 202.

The sample end plate 202 includes a plurality of bare wire electrodes 240 (FIGS. 3 and 4) depending from the lower surface of the sample end plate 202 and radially aligned with respect to the center of the turntable 100 with corresponding ones of the capillary end retainers 204. Thus in the embodiment disclosed herein, there are six such electrodes 240 corresponding to the six capillary end retainers 204. The electrodes 240 are fixed by means of a rubber adhesive within a groove 242 formed on the lower side of the sample end plate 202 and are connected to a wire 244 disposed within the groove 242. The wire 244 is routed through a larger intersecting groove 246 and is likewise retained within the larger groove 246 by a suitable rubber adhesive. The wire 244 and thus the electrodes 240 are connected to one output terminal of a high voltage d.c. power supply 248 via a suitable insulated wire (not shown).

The sample end plate 202 is adapted for vertical displacement with respect to the horizontal turntable 100. Posts 250 (one of which is shown in FIG. 1) are fixed to the mounting plate 42 and in turn support linear bearings 252 that are fixed to the outer corners of the plate 202. An elevator stepper motor 254 vertically actuates a shaft 256 that is in turn fixed to the plate 202. Actuation of the stepper motor 254 accordingly raises and lowers the plate 202 between mechanical stops defining the plate 202 up and down positions.

The capillary assembly 48 also includes a manifold plate 300. The manifold plate 300 is mounted atop the posts 250 and a support post 344 and includes an arcuate edge 302 proximate the outer edge of the sample end plate 202. The manifold plate 300 supports six detection stations 320 that are aligned above a conduit or manifold 322 formed in the interior of the manifold plate 300. In the embodiment disclosed herein, the manifold 322 is in the form of an arcuate groove 323 formed into the manifold plate 300 above a larger arcuate groove 324. A bare wire electrode 325 is disposed within the arcuate groove 323 throughout the length of the arcuate groove 323. The electrode 325 exits through and is sealed within a hole (not shown) formed through the manifold plate 300 and is connected to system ground. An arcuate closing piece 326 is sealed within the larger arcuate groove 324 to close the manifold 322.

To provide access to the manifold 322 by the capillaries 200, six holes 328 (FIGS. 3 and 7) are formed through the upper surface of the manifold plate 300, the holes 328 each including a shoulder 330 reducing to a smaller diameter portion 332 of the hole 328. An annular seal 334 is fixed within the hole 328 and includes an internal taper 336 for directing the end of the capillary 200 into the manifold 322 as is described hereinbelow.

Two tubing couplings 338 and 340 (FIG. 6) are fixed within holes formed through the closing piece 326 and are in communication with the manifold 322, the tubing couplings 338 and 340 thus providing a liquid communication path with the manifold 322.

Figure 6:
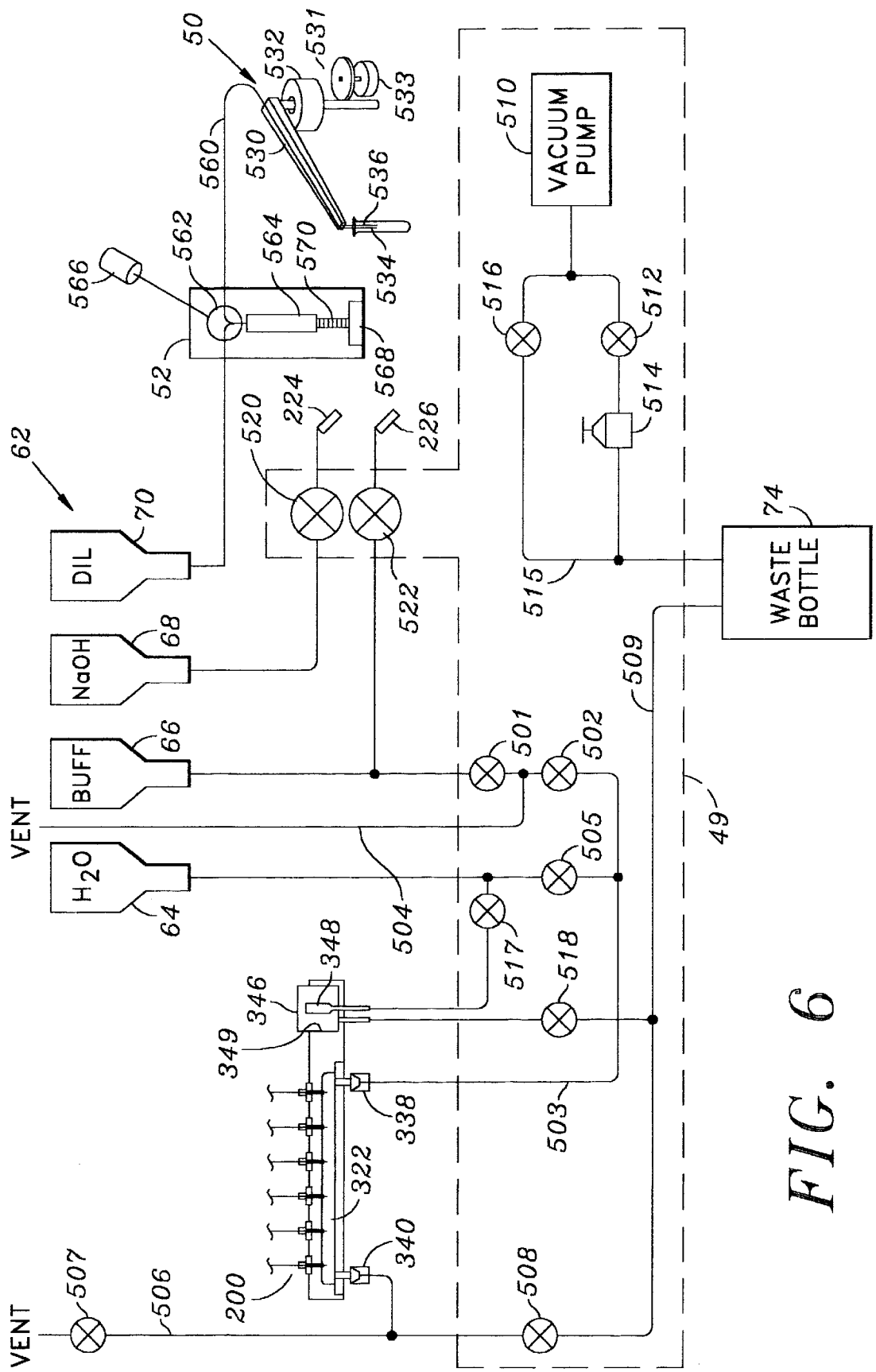
FIG. 6 is a simplified functional diagram of the fluid system of the analyzer of FIG. 1.

The manifold plate 300 also includes a wash station 346 (FIGS. 2 and 6). The wash station 346 includes an inner open-top fountain 348. Water solution may be feed through a port in the bottom of the fountain 348, overflowing the top of the fountain 348 into a catch basin 349. The catch basin 349 in turn includes a drain port through which wash effluent may be removed from the wash station 346.

The six detection stations 320 are coaxially aligned above the corresponding six holes 328 and seals 334. Each of the detection stations 320 includes vertical support structures 350 and 352 (FIG. 7) having transverse extending arms 354 and 356 with threads 358 and 360 formed on the outside of the arms 354 and 356. The vertical support structures 350 and 352 are adapted to receive the detection ends of the capillaries 200 and input and output optical fiber assemblies.

The detection end of each of the capillaries 200 is retained within a holder 400 that is formed around the capillary 200. The holder 400 includes a handle portion 402, a flattened portion 404 and a cylindrical downstream portion 406 that forms a fluid seal around the capillary 200. The downstream portion is adapted to be received by the seal 334 to establish a sealing relationship between the downstream portion 406 and the seal 334.

In the analyzer 40 of the present invention, light for the detection of the sample constituents within the capillaries 200 is brought to the capillaries 200 by fiber optics and is lead from the capillaries 200 to suitable detectors by means of fiber optics. More particularly, a single deuterium lamp within a heat sink housing 420 (mounted beneath the mounting tray 44 as shown in phantom in FIG. 1) is directed to a single optical fiber light guide 422 (FIG. 3) which is in turn split at an optical fiber splitter 424 into six input optical fiber light guides 426.

Figure 3:
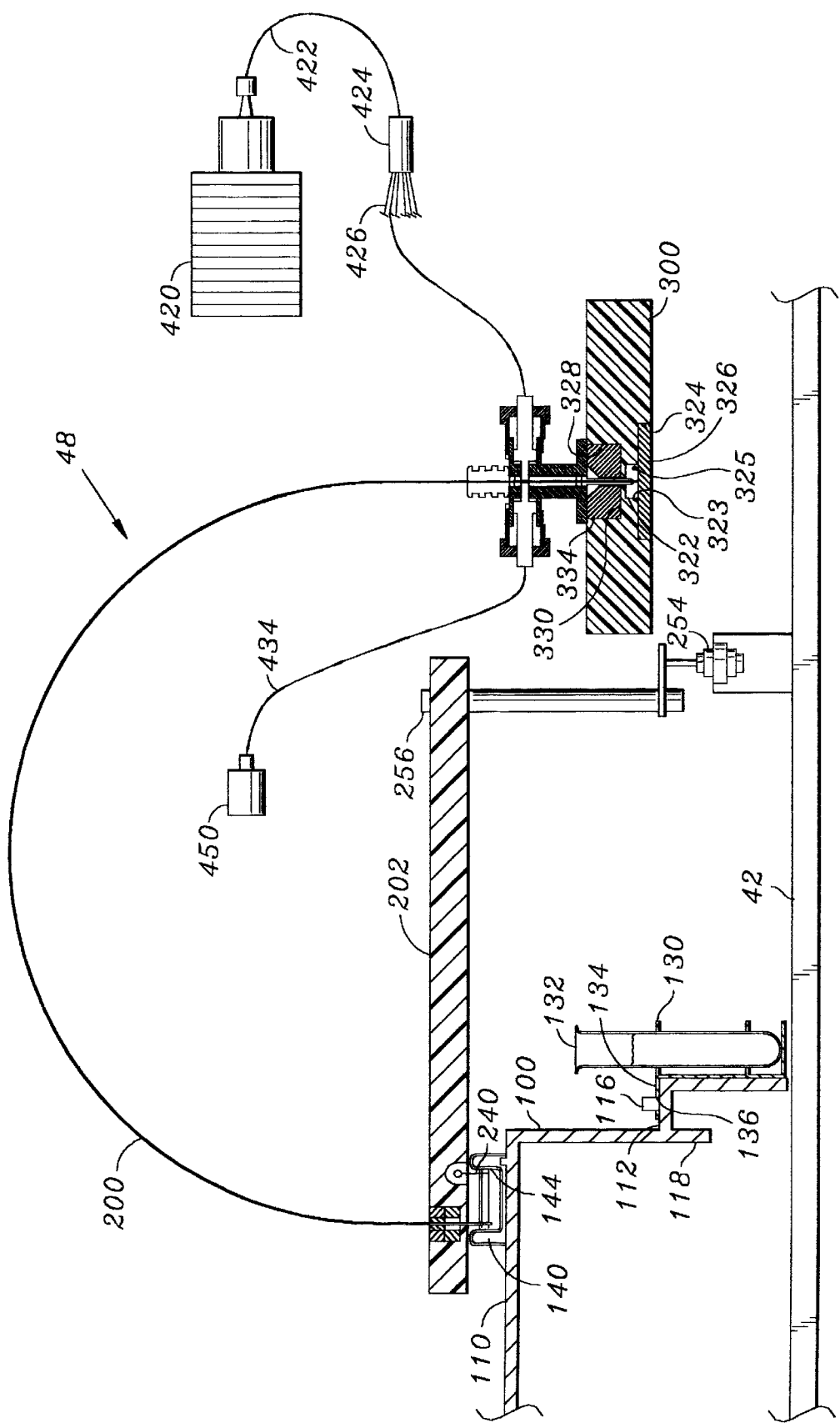
FIG. 3 is a partial section view taken along line 3—3 of FIG. 2.
Figure 7:
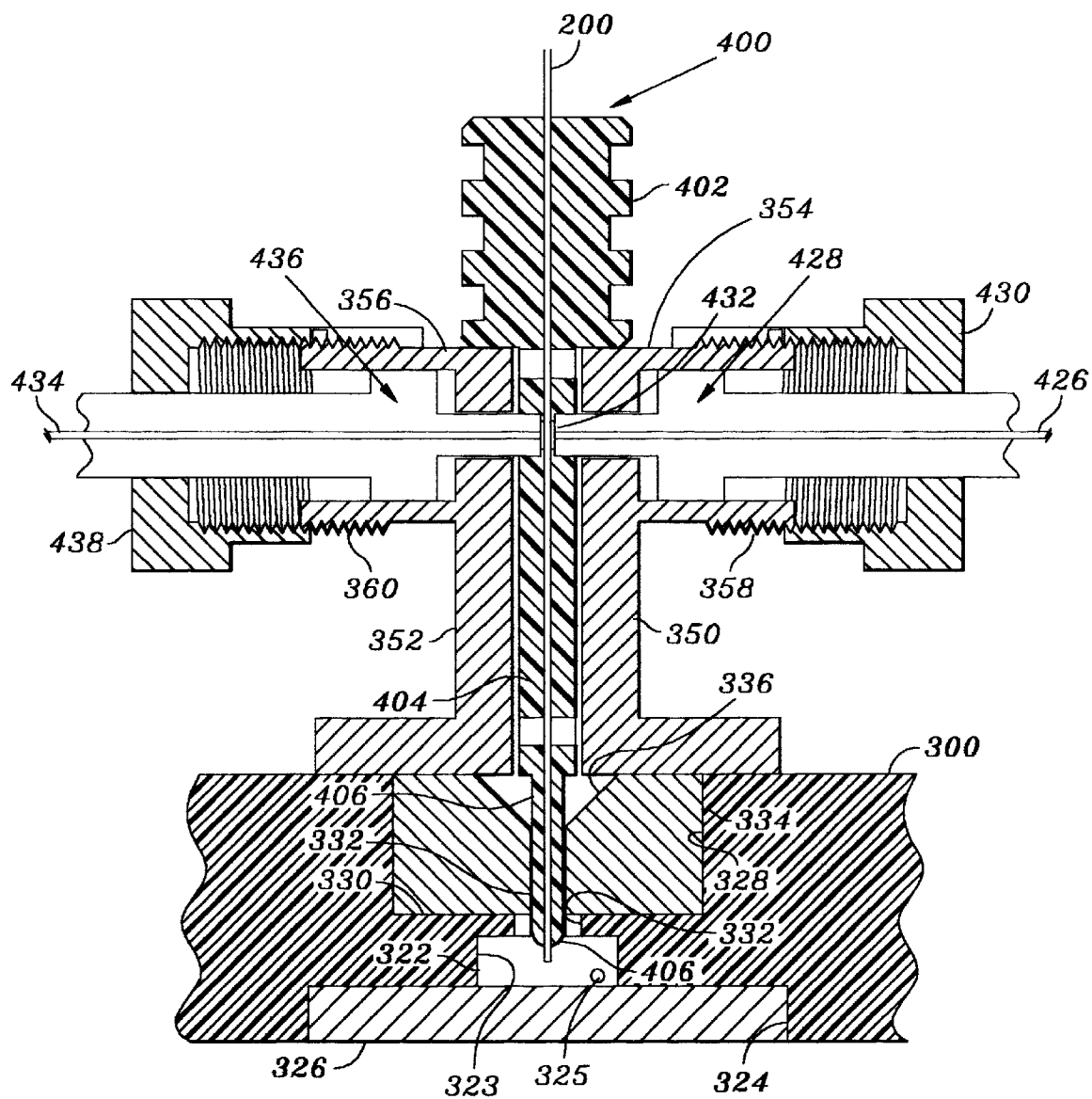
FIG. 7 is a cross-section view of a detection station for the detection end of capillaries.

Continuing the description with respect to one of the light guides 426 as seen in FIGS. 3 and 7 and it being understood that the remaining light guides 426 have corresponding structure, the input optical fiber light guide 426 terminates in a holder mechanism 428 and includes a nut configuration 430 that is removably fastened onto the arm 354. The holder mechanism 428 is positioned with respect to a window 432 formed into the flattened portion 404 of the holder 400, exposing the capillary 200. Preferably, the coating on the capillary 200 is removed to allow the passage of UV light from the end of the input optical fiber light guide 426 through the capillary to an output optical fiber light guide 434. The window and a technique for making the window are described in U.S. patent application Ser. No. 07/917,640, now U.S. Pat. No. 5,312,535, entitled Capillary Electrophoresis Detection, in the names of Waska, Klein and Johnson, filed concurrently herewith, and which is incorporated herein by reference. Although the window and technique for making the window are preferrably the same as that described in such application, other techniques for removing the capillary coating can be used.

Figure 8:
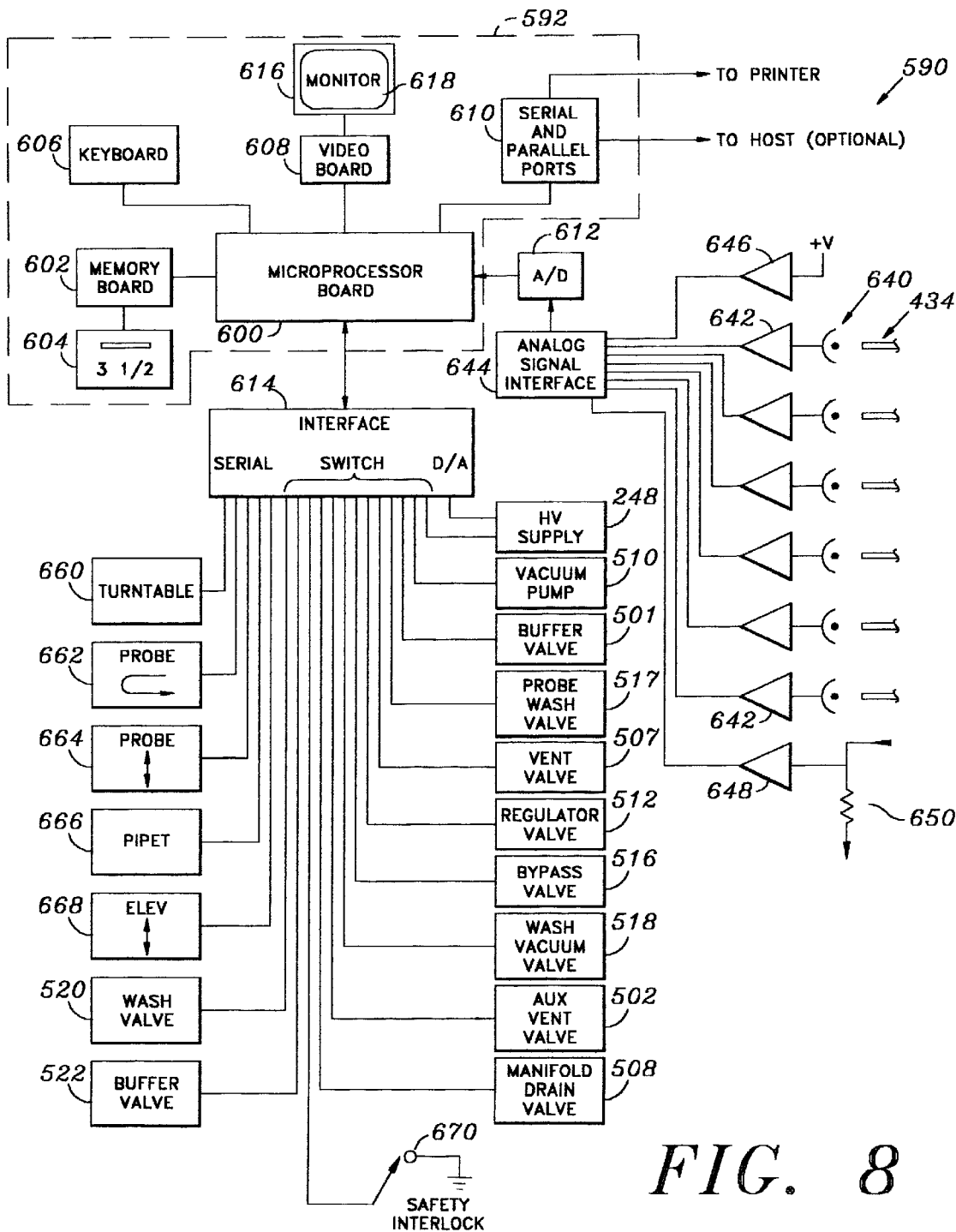
FIG. 8 is a block diagram of the control system and electronics of the analyzer of FIG. 1.

The output light guide 434 includes at its end a holder mechanism 436 which may be removably fixed within the arm 356 by means of a nut configuration 438. The opposite end of the output optical fiber light guide 434 is applied to a detector housing 450 that includes a suitable detector, such as a silicon photo-detector 640 (FIG. 8) to detect the light that passes through the capillary 200.

The fluid control system of the analyzer 40 includes the reservoirs 62, capillary assembly 48 (including the sample end plate 202 and the manifold plate 300), fluid control assembly 49, probe assembly 50, pipettor-dilutor assembly 52, and the waste bottle 74, as well as tubing interconnecting these elements. Such tubing described herein is not shown in FIGS. 1, 2 and 3 for the sake of simplicity but is instead shown in schematic form in FIG. 6. With reference to FIG. 6, the water bottle 64, buffer bottle 66, wash solution bottle 68, diluent bottle 70, waste bottle 74, wash station 346 and manifold 322 are connected to the fluid control assembly 49. The fluid control assembly 49 includes a buffer valve 501 and an auxiliary vent value 502 connected between the buffer bottle 66 and one end of the manifold 322 via a manifold line 503 and the tubing coupling 338. A vent tube 504 is connected between the valves 501 and 502 and has an open end. A water valve 505 is connected between the water bottle 64 and the tubing coupling 338 via the manifold line 503.

The coupling 340 in the second end of the manifold 322 is connected to a vent tube having an open end. A manifold vent valve 507 provides a valving function in the vent tube 506 near the open end of the vent tube 506. The open ends of the vent tubes 504 and 506 are above the level of the highest fluid in either the buffer bottle 66 or the water bottle 64 to avoid reagent spillage through either of the vent tubes 504, 506 if a valve failure should occur. The coupling 340 is also connected to a manifold drain valve 508 which in turn is connected to the waste bottle 74 via a mainfold drain line 509.

The vacuum for the fluid system is developed by a vacuum pump 510, part of the fluid control assembly 49. The vacuum output from the vacuum pump 510 is connected to one side of a valve 512, the other side of which is connected to a vacuum regulator 514. The regulated output of the vacuum regulator 514 is connected to the waste bottle 74 via a vacuum source line 515. A regulator bypass valve 516 is connected between the vacuum output from the vacuum pump 510 and the vacuum source line 515. The regulator 514 is provided to achieve a controlled vacuum that is used, for example, for drawing sample into the sample ends of the capillaries 200. The regulator 514 is bypassed by the valve 516 when less precise fluid control is needed, such as in simply drawing wash or buffer reagent through the capillaries 200 as is described below with respect to the operation of the analyzer 40.

A probe wash valve 517 is connected between the water bottle 64 and the inner fountain 348 of the wash station 346 and a wash vacuum valve 518 is connected between the drain port of the catch basin 349 and the manifold drain line 509. The valves 501, 502, 505, 507, 508, 512, 516, 517, and 518 are all solenoid-controlled valves and all but valve 507 are normally closed, that is, the valve is closed when the solenoid is deenergized or inactivated, and open when the solenoid is energized or activated. Valve 507 is normally opened.

Thus it is seen that the manifold line 503 is in common with the valves 502 and 505 and the coupling 338. On the other hand, the manifold drain line 509 is in common with the manifold drain valve 508, wash vacuum valve 518, and the waste bottle 74.

A solenoid controlled wash solution valve 520 is connected between the NaOH wash solution bottle 68 and the tube 224 included in the group of reagent dispensing tubes 230. Similarly, a solenoid controlled normally closed buffer valve 522 is connected between the buffer bottle 66 and the tube 226 included in the group of reagent dispensing tubes 230. All of the valves described to this point, but for the manifold vent valve 507, may be included in the fluid control assembly 49, and the valve 507 may be mounted on the upper tray 44 adjacent the open end of the vent tube 506.

The probe assembly 50 may be of a conventional design and includes a probe arm 530 which at one end is supported by a displacement mechanism 532 and at the other end supports a fluid conducting probe 534 and a needle 536. The needle 536 is used by the analyzer control circuitry (elevator controller 668 described with reference to FIG. 8) to detect the level of fluid as, for example, by sensing conductivity of the fluid into which the probe 534 and needle 536 come into contact.

The displacement mechanism 531 includes a vertical displacement motor 532 and a horizontal displacement motor 533 which together are controlled to lift and rotate the probe arm 530 and the probes 534 and 536 all in a conventional fashion.

The pipettor-dilutor assembly 52 is connected via fluid carrying tubing 560 to the fluid conducting probe 534. The conduit 560 is connected to a rotary valve 562 that connects a motor driven pipette 564 to either the diluent bottle 70 as shown in FIG. 6 or to the fluid conducting probe 534 as shown in the alternate valve position in phantom in FIG. 6. The valve 562 is controlled by a motor 566 and the pipette is controlled by means of a motor 568 connected through a screw drive mechanism 570 to the pipette 564. The pipettor-dilutor 52 is of a conventional design and may be, for example, model XL3000 available from Cavro (Sunnyvale, Calif., U.S.A.).

The analyzer 40 further includes a computer-based control system 590 to control the automated features of the analyzer 40 and to provide a suitable user interface. In the embodiment disclosed herein, and as illustrated in block form in FIG. 8, the computer control system 590 includes a central computer 592 which includes a microprocessor board 600. The microprocessor may be, for example, a type i386 available from Intel Corporation. The microprocessor board 600 is interfaced with a memory board 602 and in turn floppy and hard disk drives 604. The microprocessor board 600 is also interfaced with a keyboard 606, video board 608, serial and parallel ports 610, analog-to-digital converter 612, and an interface 614. The video board 608 in turn drives a conventional computer color monitor 616 having a display screen 618. It is to be understood that the computer 592 may take the form of a conventional IBM compatible personal computer (IBM is a trademark of International Business Machines Corporation) of the type very well known in the art. Further, the converter 612 and interface 614 can interface with such a computer via one or more cards that plug into the computer bus, all in a conventional fashion.

With respect to the analog portion of the control system and as described previously, output optical fiber light guides 434 are directed towards six solid state detectors 640. The output of the detectors 640 are in turn applied to six respective amplifiers 642 whose outputs are applied to an analog signal interface 644. The signal interface 644 selects the signal and scales the selected signal for analog-to-digital conversion. The selected analog output is applied to the analog-to-digital converter 612. A reference voltage amplifier 646 is also applied to the signal interface 644 for calibration of the analog signal interface 644 and the analog-to-digital converter 612.

A current monitoring resistor 650 is placed in series in the high voltage circuit formed by the high voltage power supply 248 and the capillaries 200. An amplifier 648 senses the voltage across the resistor 650 and the output of the amplifier 648 is applied to the analog signal interface 644 to thus provide a means to monitor the current through the capillaries 200.

Under the control of the microprocessor board 600, the interface 614 provides several serial data interfaces as well as switched outputs and digital-to-analog outputs for the sensing and control of assemblies and devices in the analyzer 40. Serial interfaces are provided to a turntable motor controller 660, a probe horizontal displacement motor controller 662, a probe vertical displacement motor controller 664, a pipettor-dilutor motor controller 660, and an elevator stepper motor controller 668. The motor controllers 660, 662, 664, 666 and 668, along with conventional sensing devices of the related controlled devices, control the respective motors all in a conventional fashion.

The interface 614 also includes a digital-to-analog converter that provides a voltage control signal to the high voltage power supply 248 to thereby adjust the voltage produced by the power supply 248. The interface 614 also includes switched outputs which switch on and off the high voltage power supply 248, the vacuum pump 510 and the solenoid operated valves 501, 502, 507, 508, 512, 516, 517, 518, 520 and 522. The interface 614 is responsive to a safety interlock switch 670 which is actuated when the analyzer 40 panels (not shown) are removed, thereby disabling the high voltage power supply 248 by means of the microprocessor board 600.

For the purpose of the following description of an analysis cycle of the analyzer 40, it is assumed that the analyzer 40 is in a ready state with the fluid probe 534 primed with diluent and raised to a park position above, for example, the wash station 346. Priming may be accomplished, for example, by drawing diluent into the pipettor-dilutor 52 from the diluent bottle 70, changing the position of the valve 562 to that shown by the dashed line in FIG. 6, and expelling diluent into the line 560 until the fluid probe 534 is primed. The sample end plate 202 is also raised such that the sample ends of the capillaries 200 and the electrodes 240 clear the tops of reagent segments 140 that may be carried by the turntable 100, the turntable 100 is in a home position, vacuum pump 510 and high voltage power supply 248 are off, and all valves are in the normal or deenergized state.

Before the analysis cycle begins, it is also assumed that a sample tube sector 130 is placed onto the turntable 100 at, for example, a load position 680. The sector 130 holds six sample tubes 132a through 132f, each containing a suitable sample for analysis, such as human blood serum. Also, an empty, clean reagent segment 140 is placed onto the turntable at the load position 680 inboard from the positioned sector 130 over the corresponding one of the ribs 114. For the purpose of this description, the six reservoir groups 142 in the reagent segment 140 at the load position 680 are identified as groups 142a through 142f corresponding to the six sample tubes 132a–132f, and the four reservoirs 144 in each of the groups 142a–142f are identified as reservoirs 144a through 144d.

The keyboard 606 is operated to define a capillary electrophoresis analysis cycle. Instructions given by way of the keyboard 606 to the control system 590 may include, for example, the location of the sample sector 130 on the turntable 100, the number of sample tubes 132 on the sample sectors 130 (in this example, six sample tubes 132a–132f), and the analysis parameters for each batch analysis performed with respect to the sample tubes 132 carried on a sample sector 130. The analysis parameters may include whether samples are to be drawn into the capillaries 200 by vacuum or by application of high voltage, the length of time for such sample injection into the capillary 200 ends, the voltage to be applied during electrophoresis, and the length of time that electrophoresis is to be performed.

The analyzer 40 is commanded to begin the specified analysis by way of the keyboard and the control system takes over automated control of the analyzer 40. Turntable 100 is rotated to position the first sample tube 132a under the hole 222 and beneath the arc described by the fluid probe 534. The probe 534, in an initial raised park position, is rotated to a position above the first sample tube 132a. The probe assembly 50 and the pipettor-dilutor assembly 52 are controlled to lower the tip of the fluid probe 534 into the sample contained within the sample tube 132a, draw a predetermined volume of sample into the fluid probe 534, raise the probe 534 and rotate it above the first reservoir 144a of the reservoir group 142a inboard from the sample tube 132a, and lower the tip of the probe 534 into the reservoir 144a. The pipettor-dilutor assembly 52 is controlled to dispense the sample into the reservoir 144a and also dispense an additional volume of diluent into the reservoir 144a.

The probe 534 is raised, rotated and lowered into the inner fountain 348 of the wash station 346. Typically, to wash the probe, the wash valve 517, wash vacuum valve 518, and bypass valve 516 are opened, and the vacuum pump 510 is operated to flow water into the fountain 348 around the probe and remove waste liquid via the drain port in the catch basin 349. Additional diluent may be flowed from the probe 534 into the fountain 348 by operation of the pipettor-dilutor assembly 52 to assure internal cleaning of the fluid probe 534.

As an alternative, the above sample dilution cycle can be repeated but with the probe assembly 50 and the pipettor-dilutor assembly 52 controlled to draw the first dilution of the sample from the reservoir 144a into the fluid probe 534, transfer such first dilution to the fourth reservoir 144d and add a predetermined amount of diluent to the fourth reservoir 144d through the fluid probe 534. In this way, a second dilution of the sample is created for use in the electrophoretic analysis or in a second electrophoretic analysis of the sample.

The turntable 100 is rotated to position reservoirs 144b and 144c within the reservoir group 142a beneath the wash and buffer reagent tubes 224 and 226, respectively. Valves 520 and 522 are opened for a predetermined time period to dispense running buffer and wash solution into the reservoirs 144b and 144c, respectively.

The above sample, running buffer and wash solution dispensing procedures are repeated for the remaining samples in the sample tubes 132b–132f to dispense diluted sample, running buffer and wash solution into respective reservoirs 144a, 144b, and 144c, respectively, in the reservoir groups 142b through 142f.

Assuming that the capillaries 200 are not filled with running buffer, the turntable 100 is rotated so as to position the sample ends of the capillaries 200 above the reservoirs 144b in the reservoir groups 142a through 142f that contain running buffer. The elevator stepper motor 154 is controlled to lower the sample end plate 202 until it rests atop the pins 115 and the sample ends of the capillaries 200a through 200f as well as the corresponding electrodes 240 are lowered into the running buffer reservoirs 144b of the reservoir groups 142a through 142f, respectively. The vacuum pump 510 is operated and the regulator bypass valve 516 is opened to produce a vacuum through the waste bottle 74 and the manifold drain line 509. Manifold vent valve 507 is closed and manifold drain valve 508 is opened, applying vacuum to the manifold 322, thereby drawing running buffer through the capillaries 200. After a suitable predetermined time period, the vacuum pump 510 and valve 516 are deactivated. The buffer valve 501, auxiliary vent valve 502, and manifold vent valve 507 are opened and the drain valve 508 is closed to complete the filling of the manifold 322 with running buffer by gravity feed from the running buffer bottle 66. It is much more time efficient to fill the manifold 322 with running buffer by means of gravity feed rather than attempting to fill the manifold 322 with running buffer delivered through the capillaries 200 because of the extremely small inside diameter of the capillaries 200 and the corresponding very low liquid flow rates through those capillaries, even with a vacuum applied via the waste bottle 74 by means of the vacuum pump 510 and valve 516.

With the manifold 322 filled, buffer valve 501 and auxiliary vent valve 502 are closed. Because the manifold 322 is filled with buffer by gravity feed, a fluid column is supported within the vent tube 506 essentially to the level of the buffer within buffer bottle 66. This fluid column creates a hydrostatic back pressure in the manifold 322 that can slow the separating flow of samples through the capillaries and cause run-to-run variations is separation time. To prevent this, the vacuum pump 510 is operated, and bypass valve 516, manifold drain valve 508 and manifold vent valve 507 are opened to draw or sip this fluid column into the waste bottle 74 and eliminate the potential for back pressure, normalizing the fluid pressure in the manifold essentially to atmospheric or ambient pressure and thus the same pressure on the reservoirs 144.

Alternatively, the capillaries 200 may be filled prior to the commencement of the analysis cycle. This can be accomplished by positioning a reagent segment 140 onto the turntable 100, filling the reservoirs 144b in the reservoir groups 142a through 142f of the segment 140 with running buffer, and operating the elevator stepper motor 254, vacuum pump 510 and vacuum valve 516, and the buffer, vent and drain valves 501, 502, 507 and 508 in a fashion similar to that just described.

In order to load sample into the capillaries 200, the elevator stepper motor 254 is controlled to raise the sample end plate 202 such that the ends of the capillaries 200 and the electrodes 240 clear the reagent segments 140. The turntable 100 is rotated to position the sample ends of the capillaries 200 above the sample reservoirs 144a within the respective reservoir groups 142a through 142f and the elevator stepper motor 254 is controlled to lower the sample end plate 202 onto the pins 115 such that the sample ends of the capillaries 200 are within the diluted sample contained within the sample reservoirs 144a. The vacuum pump 510 and valves 512, 507 and 508 are operated to apply regulated vacuum to the manifold 322. By appropriate timing of the application of the regulated vacuum to the manifold 322, a predetermined volume of diluted samples from the six reservoirs 144a in the reservoir groups 142a–142f are drawn to the six respective sample ends of the capillaries 200a–200f.

The vacuum pump 510 and valves 512, 507 and 508 are then de-energized to release the regulated vacuum, and the sample end plate 202 is raised, turntable 100 is rotated and sample end plate 202 is again lowered to position the sample ends of the capillaries 200a–200f and the corresponding electrodes 240 into the running buffer reservoirs 144b within the respective reservoir groups 142a through 142f.

The high voltage power supply 248 is commanded to apply a high voltage across the capillaries 200. More particularly, the high voltage power supply is connected to the wire 244 which is turn connected to the six electrodes 240 that are now disposed within the buffer reservoirs 144b. The other polarity developed by the high voltage power supply 248 is connected via system ground to the manifold electrode 325 disposed within the manifold 322. By the application of this voltage, preferably in the range of approximately 6000 to 10,000 volts DC, capillary electrophoresis begins with the samples previously drawn into the sample end of capillaries 200.

With the electrophoresising voltage applied across the capillaries 200, electrophoretic separation occurs and during the electrophoresising period of, for example, two minutes to four minutes, separated samples (depending upon the mobility of the molecules in the samples) flow past the windows 432 within each of the capillaries 200. The light directed through the windows 432 between the input and output optical fiber optic light guides 426 and 434 and thus through the bores of the capillaries is periodically sampled and processed by the detectors 640, preamplifiers 642, analog signal interface 644, analog-to-digital converter 612 and the microprocessor board 600 to create digital values related to the absorbance of the sample constituents. Preferably, the values are arranged and stored for each of the capillaries 200a–200f creating six channels or arrays of data corresponding to the six capillaries 200a–200f. The values may is stored as files on one of the disk drives 604 for further manipulation and data analysis and reduction by the control system 590 or external "host" computing means.

After the sample analysis is completed and the required data is collected by the system controller, the microprocessor board 600 controls the high voltage power supply 248 to remove the electrophoresising voltage from the capillaries 200. The elevator stepper motor 254 is actuated to raise the sample end plate 202 such that the sample ends of the capillaries 200 and the electrodes 240 clear the reagent segment 140 and the turntable 100 is rotated to position the wash fluid in the reservoirs 144c beneath the sample ends of the capillaries 200. The elevator stepper motor 254 again is controlled to lower the sample end plate 202 to position the sample ends of the capillaries 200a–200f within wash solution contained in the reservoirs 144c within the reservoir groups 142a through 142f, respectively. Regulated vacuum is again applied to the manifold 322, drawing the wash solution through the capillaries 200 to the manifold 322. After a predetermined time period, the capillaries 200 are recharged with running buffer, preparing the capillaries for the next analysis. Water in the bottle 64 may be used, for example, for maintenance washing of the manifold 322 when the analyzer 40 is shut down by opening the valve 505. The capillaries 200 may be stored for a long idle period in a dry state after suitable cleaning. The vent tube 504 may be used when draining the manifold 322 via the valves 502 and 508 into the waste bottle 74 with vacuum applied.

Additional sample tube sectors 130 may be placed onto the analyzer 40 and the batch parallel analysis cycle just described may be repeated.

Thus, the analyzer 40 of the present invention enables the batch parallel analysis of samples through a plurality of capillaries, the capillaries sharing a common manifold at the detection end of the capillaries. By using the common manifold, capillary electrophoresis can be performed in a reliable, efficient manner using a analyzer that does not include complicated individual fluid channels for each of the capillaries. Capillary preparation, sample loading, electrophoresising, capillary cleaning and reloading are more efficiently accomplished by means of the common manifold, and can be more simply accomplished as, for example, by the use of gravity feed or simultaneous, parallel vacuum feed. Such simplicity eliminates additional pumps, pinch valves, rotary valves and the like.

Figure 9:
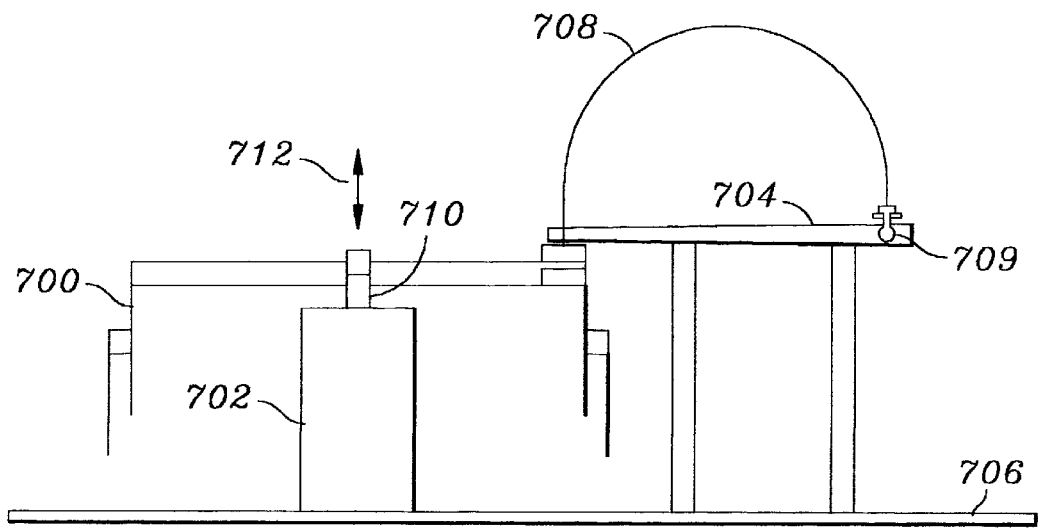
FIG. 9 is a simplified side view of another embodiment of a turntable and capillary system for use in an analyzer in accordance with the present invention.

It is to be recognized that the reagent segments 140 may be brought to the sample ends of the capillaries 200 other than by means of the elevator stepper motor 254 raising and lowering the sample end plate 202. For example, and with reference to FIG. 9, an alternative version of an analyzer in accordance with the present invention may include a turntable 700 mounted to a turntable rotational and vertical displacement mechanism 702 which is in turn supported by means of an analyzer base place 706. The mechanism includes means for raising and lowering the turntable 700, such as a vertical displacement motor and mechanism, and a rotational displacement motor and mechanism, all of conventional design. A capillary assembly 704 is fixed with respect to the base plate 706 and includes a plurality of capillaries 708 and manifold 709 essentially identical to the capillaries 200 and manifold 322. Under the control of a suitable control system similar to that described above, the mechanism 702 rotates the turntable about a shaft 710 and also vertically displaces the turntable 702 upwardly and downwardly as illustrated by the arrows 712. Accordingly, the sample ends of the capillaries 708 as well as electrodes (not shown) to provide the electrical connection may be placed into and removed from reservoirs contained in reagent segments similar to those reagent segments 140 described above. With respect to either the embodiment of the analyzer 40 or the embodiment disclosed in FIG. 9, the sample ends of a plurality of capillaries are simultaneously placed within reservoirs and reagent segments, enabling batch parallel analysis and processing of samples by the capillaries.

Other modifications to the analyzer 40 are possible. For example, the capillary assembly 48 may be disposed within a temperature controlled chamber that is heated and cooled, for example, by Peltier devices to provide a thermally stable environment in which the capillaries 200 are operated. Such a temperature stabilized environment may be particularly advantageous where the batch parallel analysis performed by the capillaries must be temperature stabilized, capillary to capillary, to thereby eliminate the effects of temperature on the results detected by the analyzer 40.

It is also to be understood that the number of capillaries 200 carried in the capillary assembly 48 may be increased or decreased according, for example, to the number of samples that may be carried by sample sectors.

Figure 10:
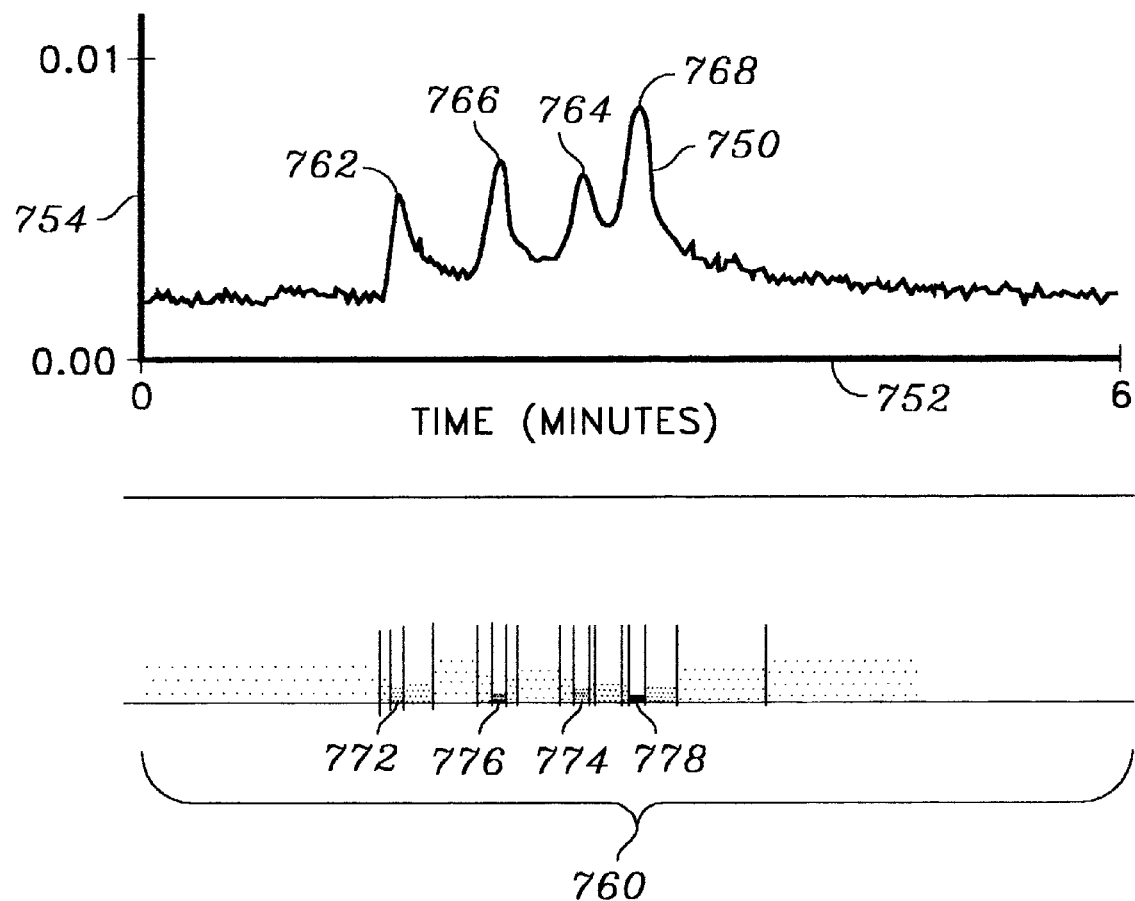
FIG. 10 is a representation of a display in accordance with the present invention.

For each of the capillaries 200, the control system 590 may display the absorbance data collected by the control system 590 as an electrophoretogram on, for example, the monitor screen 618 in a conventional form such as an electrophoretogram in the form of an absorbance graph 750 (FIG. 10). Such a representation may be, for example, a series of selected absorbance data points plotted with respect to time on a horizontal axis 752 and absorbance on a vertical axis 754 and connected by lines to form the graph 750. The time or horizontal axis 752 may illustrate electrophoresising time in a range beginning with the application of electrophoresising voltage at zero minutes to the end of the capillary electrophoresis analysis at, for example, six minutes, while the vertical absorbance axis 754 may represent absorbance in a range of 0.00 to 0.01.

In accordance with the present invention, the absorbance data collected by the control system 590 is also displayed on the monitor screen 618 in the form of a graphic stripe 760. To generate the stripe, the control system 590 determines the relationship between a selected absorbance value and a range of absorbance values. Using this relationship, the control system 590 selects a graphic value from a range of graphic values and displays the selected graphic value. Preferably, the selected absorbance value corresponds to an absorbance data point plotted in graph 750 and the selected graphic value is horizontally aligned with such absorbance data point. By performing this process for each of the data points displayed in the graph 750, the control system 590 generates the stripe 760. The stripe 760 thus uniquely visually represents varying absorbance as a stripe of graphic values with respect to electrophoresising time. Such a display provides to one interpreting the capillary electrophoretic data, such as a pathologist in a clinical chemistry laboratory, both a quantitative (by way of the graph 750) and qualitative (by way of the stripe 760) view of the capillary electrophoresis absorbance data.

The range of graphic values may be any range, scale or spread of visual or graphic representations that provides a visually differing display over the range, scale or spread. Such a range may be formed for example by differing hue, saturation, and/or brightness, or may be a monochrome range of values, perceived as a brightness range from light to dark or, conversely, from dark to light for increasing absorbance. The range may also be formed by dithering techniques to create an apparent range of color or intensity. In the embodiment disclosed herein, the range of graphic values is a range of colors from for example at one extreme, white, corresponding to the minimum absorbance that may be displayed by the graph 750 and for the display of FIG. 10, an absorbance of 0.00, to saturated blue for the highest absorbance that may be displayed by the graph 750 which for the display of FIG. 10 is an absorbance of 0.01. Thus, when viewed in color on the screen 618, the stripe 760 is composed of a range of colors from white through light blue to deep blue according to the corresponding absorbance shown on the absorbance graph 750. The diagrammatic representation of FIG. 10 depicts the stripe 760 as a monochromatic gray scale, the white end of the gray scale corresponding to white on the screen 618, and the darkest gray on the gray scale corresponding to most saturated blue on the screen 618.

As seen in FIG. 10, for example, peaks 762, 764, 766 and 768 represent increasing absorbance on the graph 750. Corresponding bands 772, 774, 776 and 778, respectively, serve to visualize increasing dark graphic values in the stripe 760 with respect to the increasing absorbance peaks 762, 764, 766 and 768.

As noted above, the graphic value selected from the graphical range of values scale is horizontally aligned with respect to the corresponding absorbance. For example, the absorbance peak value 762 is horizontally aligned (left to right alignment, one above the other as viewed in FIG. 10) directly above the corresponding darkest graphic value within the band 772. Similarly, the absorbance peaks 764, 766 and 768 are horizontally aligned directly above with the corresponding darkest graphic values within the respective bands 774, 776 and 778.

Figure 11:
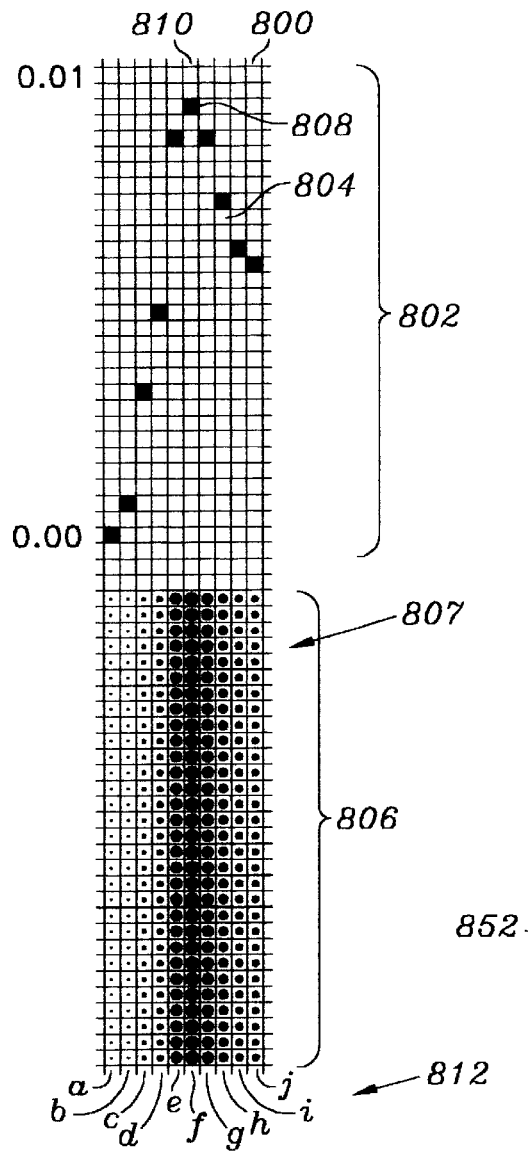
FIG. 11 is an enlarged diagrammatic representation of display pixels illustrating a graph of absorbance data and a graphic representation according to the present invention correlated to such absorbance data graph.

A diagrammatic representation of an absorbance graph and a corresponding stripe representation is seen in FIG. 11. The video board 608 and the monitor 616, for example, produces a display by arranging display screen 618 pixels in rows and columns as is well known in the art. The pixels on the screen 618 are presented in FIG. 11 by a plurality of squares 800 arranged in rows and columns. A first group of thirty rows of the pixels 802 is controlled to depict an absorbance graph 804. Similarly, a second group of thirty rows of pixels 806 is controlled to create a stripe representation 807 in accordance with present invention. For this example, it is assumed that the absorbance range which may be depicted in the group 802 is 0.00 to 0.01.

To represent the color of pixels on the display screen, the pixels in the first group 804 are shown in a square form in FIG. 11, filling the pixel, to represent the screen color shown on the screen 618. For example, the squares may correspond to the color red on the screen 618, although other colors could be used.

In this example, is it assumed that the range of graphic values to be displayed on the screen 618 in the second group 806 is from white for the minimum absorbance to saturated blue for the maximum absorbance. To represent the range of graphic values in FIG. 11, the range is depicted by no dot in the pixel or square 800 for the white end of the range to a dot filling the pixel for the saturated blue end of the range.

To obtain the display illustrated in FIG. 11, absorbance data may be stored corresponding to each of the pixel columns 812a–812j. For example, each of the pixel columns 812a–812j may represent one second sample periods during electrophoresising. Thus, absorbance is sampled each second and stored corresponding to the columns 812a–812j. As is well known in the art, a pixel is selected having a vertical position within the group 802 in proportion to absorbance within the range of 0.00 to 0.01 and the color of the pixel is changed. This procedure is repeated to form the graph 804. The color of intermediate pixels between the pixels shown as dark blocks in FIG. 11 may also be changed to form a line, not shown in FIG. 11 for the sake of clarity. The absorbance graph 804 discloses an absorbance peak 808.

In accordance with the present invention, a graphic value from the white-to-blue range of graphic value is selected in proportion to the absorbance for the pixel column. More particularly, the absorbance is related to the absorbance range represented by the group 802 (in this example, 0.00 to 0.01) and the resulting ratio is used to proportionally select the graphic value from the range of graphic values. The pixels in the corresponding pixel column within the group 806 are then all adjusted or set to the selected graphic value. The result is a stripe having a height equal to the group 806 and a display width equal to the width of the graph 804. As can be seen in FIG. 11 the relative graphic value or "darkness" of the stripe 807 varies according to the absorbance represented by the graph 804, thereby providing both a quantitative view of the absorbance data by way of the graph 804, as well as a more qualitative view of such absorbance data by way of the stripe 807.

Figure 12:
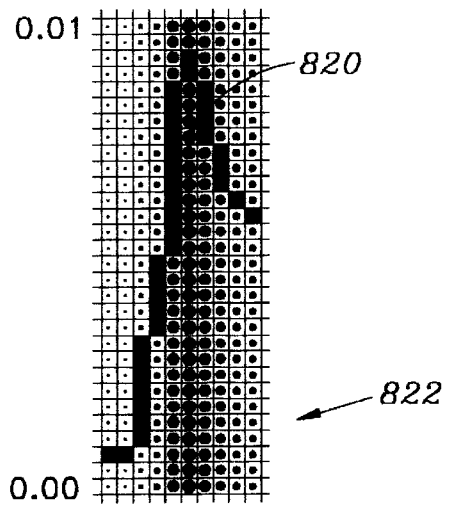
FIG. 12 is an enlarged diagrammatic representation of another embodiment of the present invention wherein the absorbance graph is overlaid with respect to the stripe.
Figure 13:
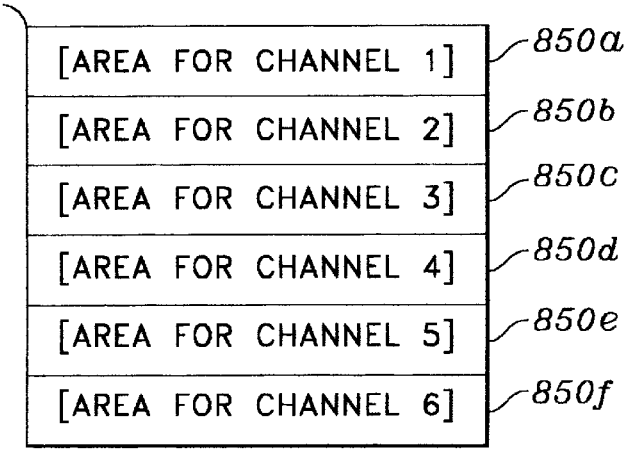
FIG. 13 is an illustration of the relative screen positions of absorbance graphs and/or simulated density stripes for the plurality of capillaries 200 in accordance with the analyzer of the present invention.

As an alternative, and as illustrated in FIG. 12, a graph of absorbance values 820 may occupy the same vertical position as does a stripe visual representation 824, providing a convenient and visually useful technique for displaying both absorbance graph and absorbance stripe representations one over the other. Furthermore, for the analyzer 40 of the present invention, absorbance data for all six capillaries 200a–200f of the analyzer 40 may be presented as illustrated in FIG. 13 on the screen of the monitor 616. Each of the capillaries 200a–200f includes its own area, 850a–850f, respectively. Each of the areas 850a–850f may display the absorbance data as a conventional absorbance graph or electrophoretogram such as the graph 759 of FIG. 10, may display the absorbance data as a stripe similar to the stripe 760 of FIG. 10, or may display a stripe overlaid with an absorbance graph similar to that illustrated in FIG. 12.

The display arrangement of FIG. 13 allows the direct comparison of the results for each of the capillaries 200. This is a particular advantage in, for example, an immunosubtraction assay such as that described in U.S. patent application Ser. No. 07/916,313 filed concurrently herewith, now U.S. Pat. No. 5,228,960, in the names of Cheng-Ming Liu, Hann-Pinn Wang, Fu-Tai A. Chen, James C. Sternberg and Gerald Klein, and entitled Analysis of Samples by Capillary Electrophoresis Immunosubtraction, and which is incorporated herein by reference. In such an assay, the same sample is analyzed through the six capillaries 200 but is acted upon by an immunoreaction prior to the electrophoretic analysis for five of the capillaries 200. The display format of FIG. 13 allows ready visual comparison of the immunosubtraction results.

An advantage of the present invention is that the stripe graphic representation can provide significant information about the character of an electrophoretogram in a limited vertical area or height on the screen 618. An electrophoretogram such as the graph 750 of FIG. 10 requires a vertical scale 754 to provide information, and generally more information is conveyed by the electrophoretogram as the height of the vertical scale 754 increases. This of course can be a disadvantage where there is limited vertical space, such as on the screen 618. However, because significant information is conveyed by a range of graphic values using the stripe of the present invention, such a range can be presented in a limited vertical height on the screen. Thus, although six areas 850a–850f are illustrated in FIG. 13, a larger number of such areas may be grouped together while still retaining the character of the information conveyed by the stripe of the present invention. This can be a particular advantage, for example, where a pathologist is quickly reviewing a number of capillary electrophoresis results, looking for overall patterns and relationships.

Figure 14A:
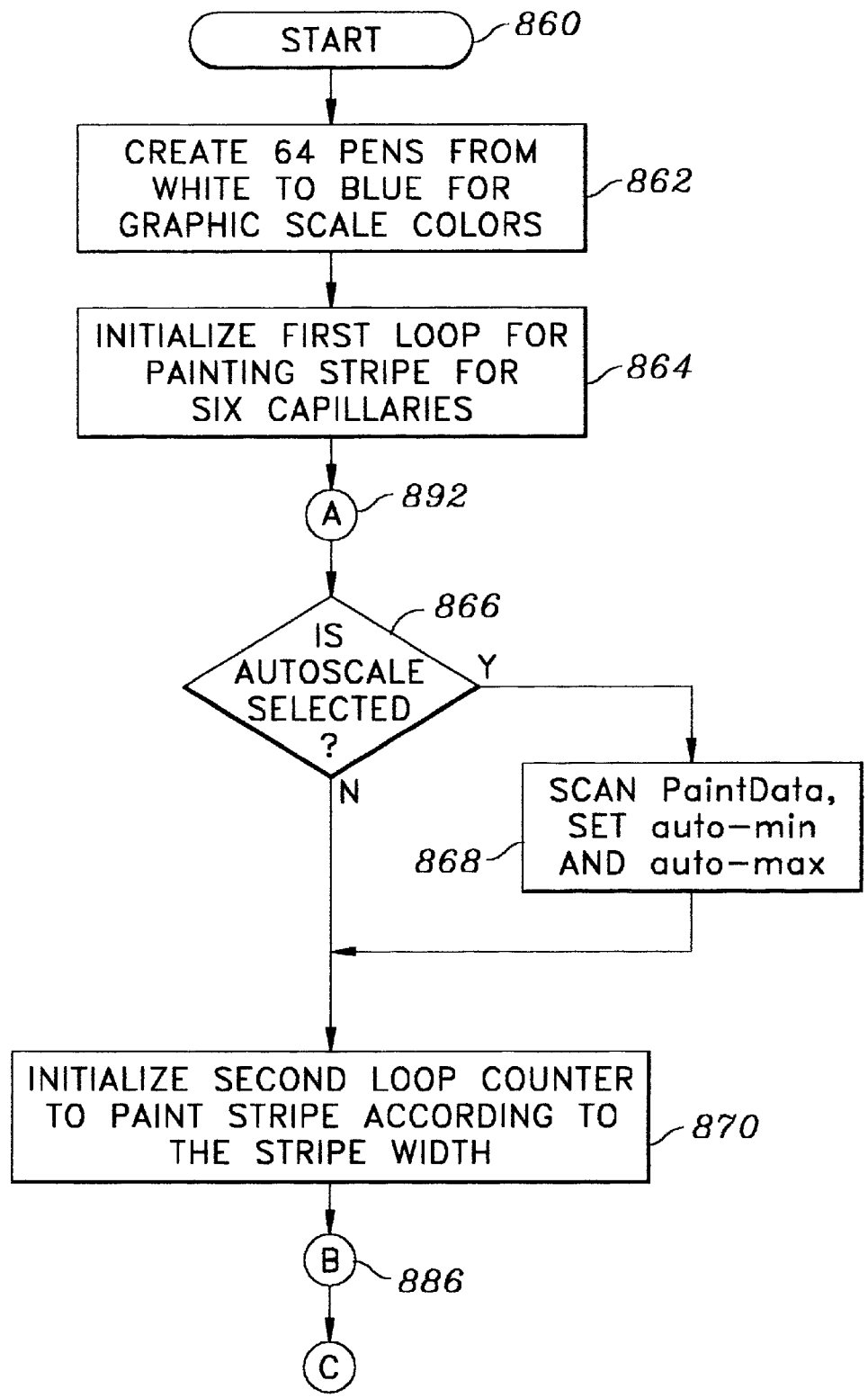
FIGS. 14A, 14B and 14C, is a block flow diagram of a method for drawing the graphic representation in accordance with the present invention.
Figure 14B:
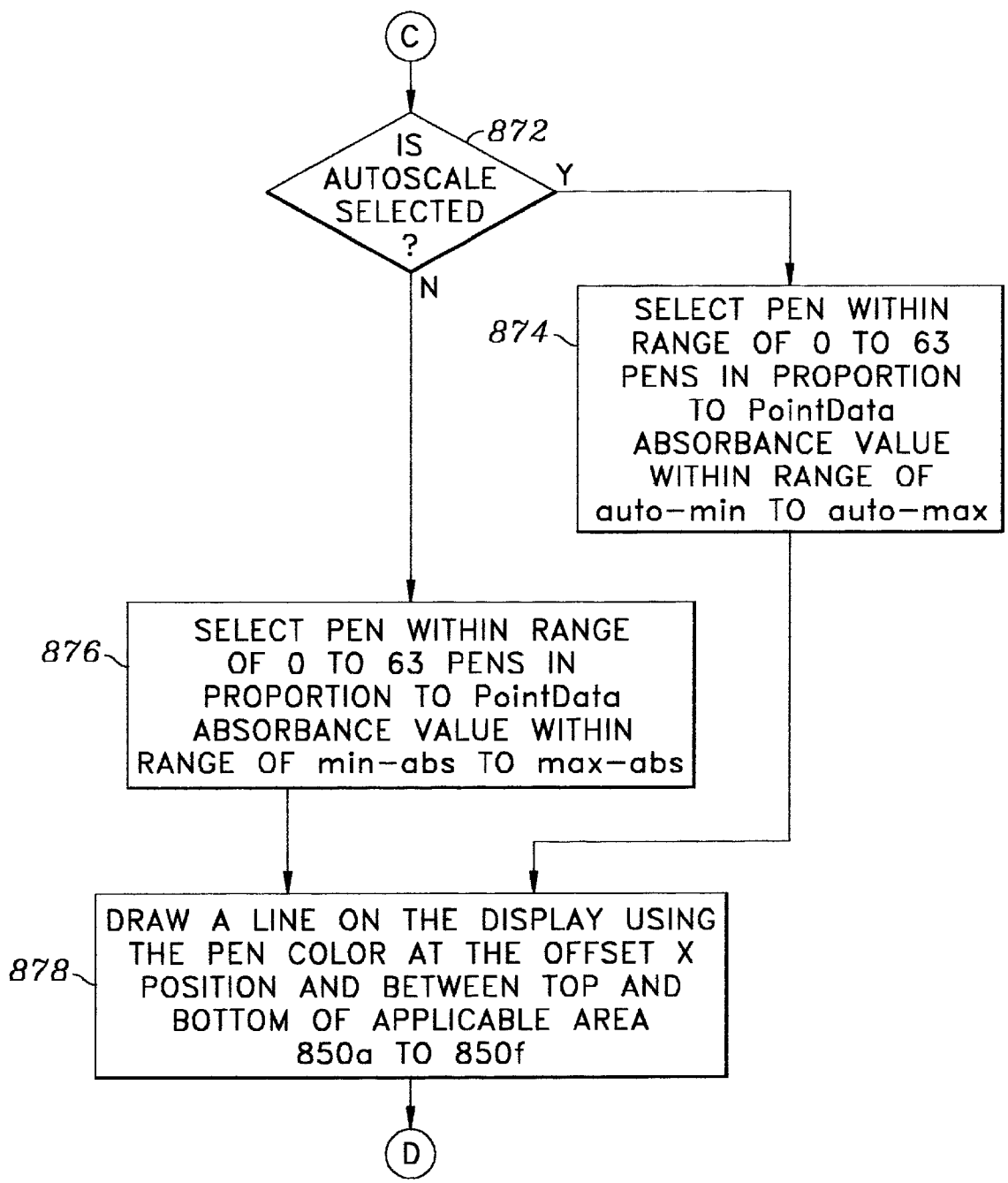
Figure 14C:
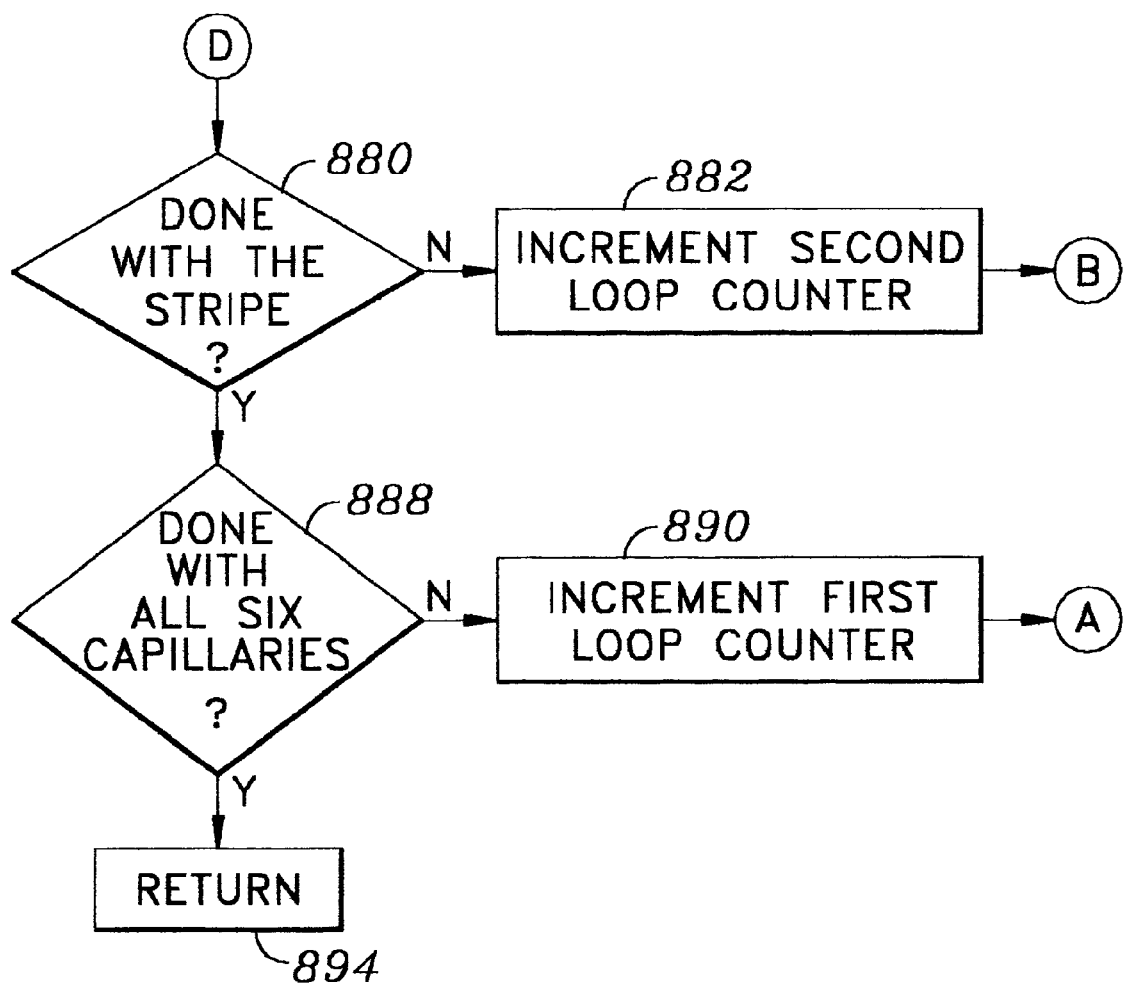

With reference to FIG. 14, a method for displaying the stripe 760 in accordance with the present invention in the format as illustrated in FIG. 13 is shown in block form. For the method of FIG. 14, a stripe width variable (stripe__width) is preset to the width of the stripe on the screen 618 in terms of pixels, and an array of absorbance data (PaintData) for each of the capillaries 200 is created, each such array having a number of elements equal to stripe__width. For example, for a standard VGA display width of 640, stripe__width is set to 520 pixels, and the PaintData arrays for the capillaries each include 520 elements. Each PaintData array is filled with absorbance data with respect to electrophoresising time for the respective capillaries 200. The absorbance data is selected from, for example, files of absorbance data points with respect to electrophoresising time created during an electrophoresis analysis by the analyzer 40, and the particular absorbance data points are selected with respect to electrophoresising time to fill the PaintData arrays over the time period to be illustrated by the stripe.

Predetermined minimum and maximum absorbance values are stored (min__abs and max__abs), set respectively to 0.00 and 0.01. Also, screen corner X (left to right) and Y (top to bottom) coordinates are established for the upper left-hand corner of the first stripe, corresponding to upper left-hand corner 852 of the area 850a for the first capillary 200a. It is to be appreciated that any order of the capillaries 200 may be used, but perferrably the order is selected to display data from capillaries 200a through 200f for the groups 142a through 142f within the areas 850a–850f, respectively.

Upon entering the method of FIG. 14 (block 860), sixty four "pens" are created from white to saturated blue for the range of graphic values (block 862). The pens, as is well known in the programming art, are red, green and blue (RGB) quantities that are arranged in a pen array (Pen) with a first element (element 0) of Pen having maximum RGB quantities to produce white, representing minimum absorbance, and a last element of Pen (element 63) having minimum RG and maximum B quantities to produce the deep blue, representing maximum absorbance. The RG quantities are stepped from the first to last element of Pen to create the smooth color change over the range of graphic values.

The method then initializes a first loop controlled by a first loop counter for painting the stripe for the six capillaries 200 (block 864), beginning with the first capillary 200a. The first loop counter selects the PaintData array to used. If an auto scaling function is selected (block 866), that is, a function or operational control that automatically scales absorbance between the maximum and minimum absorbance stored in a PaintData array for a capillary, the absorbance data in the selected PaintData array is scanned and the lowest and highest absorbance measurements in the array are used to set auto_min and auto_max variables, respectively (block 868). If auto scale is not selected, or once auto_min and auto_max are set, the method initializes a second loop controlled by a second loop counter (block 870) capable of stripe_width iterations to paint a stripe 520 pixels wide for respective elements in the PaintData array.

Continuing with the method of FIG. 14, the method again checks to determine if auto scale is selected (block 872). If auto scale is selected, a Pen array element index value or pointer is selected within the range of Pen array elements of 0 to 63 pens in proportion to the PaintData absorbance value within the range of auto_min to auto_max (block 874). On the other hand, if auto scale is not selected, a Pen array element is selected in proportion to the PaintData absorbance value within the range of min_abs to max_abs (block 876). In either case, the selected Pen index value indexes or points to a Pen array element that has a graphic value within the range of graphic values stored in Pen that is proportional to the PaintData absorbance value within the applicable range of absorbance values.

As an example, if auto scale is not selected, the equation implemented by the method in block 876 to select the Pen array element index value or pointer is:

$$\text{int}\left[\frac{((\text{PaintData value}) - \text{min\_abs}) * (63 - 0)}{(\text{max\_abs} - \text{min\_abs})}\right] + \text{min\_abs}$$

A similar equation, substituting auto_min for min_abs and auto_max for max_abs is implemented when auto scale is selected (block 874).

After completing the steps of either block 874 or 876, a line is drawn on the display screen 618 using the selected pen color from Pen at an X (left to right) position offset from the screen corner X position by the second loop counter, and between the top and bottom of the area 850a–850f that is being painted with the stripe. For example, if the first capillary 200a absorbance data is being painted into the area 850a, then the line of selected Pen array color is drawn at the offset X position between the top and bottom of the area 850a. The beginning screen Y position for this line may be calculated, for example, by starting with the screen corner Y position, offset with an amount equal to the first loop counter multiplied by the stripe height in pixels. The length of such a line is the height of one of the areas 850a–850f which are may all be equal.

The method then checks to determine whether the stripe is completed (block 880) by testing the second loop counter (block 870). If not, the method increments the second loop counter and loops back to the top of the stripe width loop at label B (884).

On the other hand, once the stripe is completed and the stripe width loop (block 870) is satisfied, the method then checks to determine whether the six capillary first loop (block 864) is satisfied and thus the method is done with all six capillaries 200 (block 888). If not, the method increments the first loop counter and loops to label A at the top of the first loop (892). On the other hand, if the method has drawn the stripe for all six capillaries 200, then the method returns to the calling function (step 894).

Preferably, the method of FIG. 14 may be implemented in the C programming language, utilizing Windows graphic users interface window environment (Microsoft Corporation, Redmond, Washington, U.S.A.) using programming techniques well known in the art. Further, although the central computer 592 may both control the analyzer 40 and provide the operator interface and graphic display functions just described, a preferred embodiment of the present invention performs the user interface and graphic display functions on a separate computer communicating with the central computer 592 via a serial port within the serial and parallel ports 610. In this instance, such a computer is a "host" computer.

With the stripe graphic representation of the present invention implemented in a window environment, each of the areas 850a–850f of FIG. 13 may as an alternative occupy an individual window on the screen 618. Because such windows are typically movable about the screen 618 and can be individually opened and closed, the areas 850a–850f may be individually moved about the screen 618 and grouped as the user may desire to compare results, for example, between selected ones of the capillaries 200 for a single parallel analysis, or between the results for different parallel analyses.

The graphic values displayed according to this invention can be enhanced or emphasized to add visibility, for example, to lightly colored portions of the stripe 760. This can be accomplished by decreasing max_abs by a predetermined amount such as ten percent (10%) and performing the method of FIG. 14 with auto scale disabled. With max_abs decreased, the absorbance data is related to an absorbance range that has a lower maximum, thereby selecting more saturated blue graphic values. This produces a stripe 760 that is darkened or enhanced, and produces a visual impression that is similar to an "overstained" gel obtained in the known gel electrophoresis art.

Similarly, the graphic values displayed according to this invention can be de-emphasized to show detail in the stripe 760 where high absorbance produces a dark band of graphic values. This is conversely accomplished by increasing max_abs a predetermined amount and performing the method of FIG. 14 with auto scale disabled. Because absorbance values are proportioned in an absorbance range having a higher upper limit, higher absorbance values produce graphic values correspondingly lower on the range of graphic values, thus for example lightening the resulting stripe 760 display.

It is also to be recognized that the range of graphic values may be nonlinear to emphasize or de-emphasize ranges of absorbance values. For example, the graphic values in the Pen array may be generated in a non-linear fashion to emphasize an absorbance range. Similarly, the range of graphic values may include subranges of differing hues or ranges or hues or intensity. Thus, absorbance values near the middle of the absorbance range might be represented by shades of red to provide emphasis or enhancement within such a range.

Although described herein with respect to creating a display on a computer display screen such as the screen 618, the resulting graphic values may be printed as, for example, using a laser printer and using half-tone or dithering techniques, all well known in the art, to create a monochromatic range of graphic values from which graphic values may be selected for printing. The graphic values may be printed in color on a color printer of the type well known in the art, such as an ink jet or thermal transfer type printer. Also, a monochromatic image of graphic values may be printed using a thermal printer with the print intensity varied by pulse width modulation of the heating current applied to the print head as the print head moves across the thermal sensitive paper. In these examples, the resulting printed copy, perferrably including both an absorbance graph such as the graph 750 and a stripe 760 in accordance with the present invention for one or more of the capillaries 200, provides a permanent record that may be included in, for example, a patient's medical file.

As yet another alternative, the screens generated according to the present invention may be saved as screen dump files in any one or a number of widely known and used graphic file formats, such a TIFF, PIC and the like, in varying color depth resolutions (for example 16, 32, 64, 256, etc.), and may be stored on networks or with hospital laboratory information systems for ready display through the hospital or by remote inquiry device.

Although described herein as relating to the display of absorbance data gathered in capillary electrophoresis, the invention may also be used with other capillary electrophoresis measurement techniques. For example, rather than absorbance, the present invention may be used to display fluorescence, radioactive activity or conductance measured during capillary electrophoresis as a stripe of graphic values. Thus, using fluorescense as an example, the graph 750 of FIG. 10 may represent fluorescence response measured during capillary electrophoresis and the stripe 760 then represents graphic values selected according to corresponding fluorescense from a range of graphic values related to the range of fluorescence values.

Further, although the relationship between an absorbance value and the corresponding selected graphic value has been described as linear herein, other relationships, such a nonlinear, including logarithmic, and the like are contemplated.

The present invention is not to be limited to the embodiment disclosed herein, but is to be afforded the full scope of the appended claims and all equivalents thereof.

- 49 -

APPENDIX

--- Symbol Table ---

```
a  [ 5]     type I
b  [ 6]     type I
c  [ 7]     type I
d  [ 8]     type I
e  [ 9]     type I
f  [10]     type I
q1 [ 1] +4  type R  inputs  a b c d x1
q2 [ 2] +3  type R  inputs  a b d q1 q2 x1 x2
x1 [ 3] +1  type O  inputs  a b d e f
x2 [ 4] +4  type O  inputs  a d f q1
```

Equation list
[ q1, q2, x1, x2 ]

- 50 -

```
---Pin map---

Output equation: q1
        PLE11R8 -- 9  10 11 13 14 15 16 17
         P16R4  -- 14 15 16 17
         P16R8  -- 12 13 14 15 16 17 18 19
         PLS173 --

Output equation: q2
        PLE11R8 -- 9  10 11 13 14 15 16 17
         P16R4  -- 14 15 16 17
         P16R8  -- 12 13 14 15 16 17 18 19
         PLS173 --

Output equation: x1
        PLE11R8 --
         P16R4  -- 12 13 18 19
         P16R8  --
         PLS173 -- 14 15 16 17 18 19 20 21 22 23

Output equation: x2
        PLE11R8 --
         P16R4  -- 12 13 18 19
         P16R8  --
         PLS173 -- 14 15 16 17 18 19 20 21 22 23 try_fixed( )

No output signals fixed to pins try_fixed: fail

Initial try -- place output signals on device 1 in the current solution

#1   try( 1, () )

try selects the first entry in lib_list that can contain an output signal

#2   try_device( 1, PLE11R8, [ 1] )

Initial state of the pNode and fvl list for the first device in the solution list --- Pnode ---
           | lib_index: 1
           |     pins:  . . . . . . . . . . . . . . . . . . . . . . . .
           | input list:
           --------------
```

```
                        - 51 -
        ---fvl---
        |  [ q1, AVAIL OUTPUT, -5, 0 ]
        |  [ q2, AVAIL OUTPUT, -7, 0 ]
#3      |  [ x2, ALWAYS INPUT, -4, 0 ]
        |  [ x1, ALWAYS INPUT, -5, 0 ]
        --------- fit_f selects the first output signal in fvl and places it on the device

4      fit_f( PLE11R8[1] )
5      fit_f: q1 placed on pin 9 of PLE11R8 fa list reflects q1 assigned to device 1 in the current solution

6      fa: q1:1 q2:-1 x1:-1 x2:-1 check that all must-be-inputs can be assigned

7      assign_inputs: partial
          --- Pnode ---
          |  lib_index: 1
          |     pins:  a b c d x1 . . . q1 . . . . . . . . . . . . . . .
          |  input list:  a b c d x1
          ------------- assign_inputs: inputs assigned

The new fvl reflects q1 assigned -- no avail output auxiliary signals

---fvl---
        |  [ q2, AVAIL OUTPUT, 1, 0 ]
        |  [ x1, ALWAYS INPUT, 1, 1 ]
#8      |  [ x2, ALWAYS INPUT, 0, 0 ]
        |  [ q1, ALREADY ASSIGNED, 5, 0 ]
        --------- q1 placed, return to try_device to place other output signals fit_f: placed q1 try_device makes sure all signals needed can be assigned

9      assign_inputs: final
          --- Pnode ---
          |  lib_index: 1
          |     pins:  a b c d x1 . . . q1 . . . . . . . . . . . . . . .
          |  input list:  a b c d x1
          -------------
        assign_inputs: inputs assigned
```

```
                             - 52 -
                Updated pnode and fvl list with q1 assigned --- Pnode ---
                | lib_index: 1
                |     pins:      a b c d x1 . . . q1 . . . . . . . . . . . . . . .
                | input list:    a b c d x1
                -------------
                ---fvl---
      5         | [ q2, AVAIL OUTPUT, 1, 0 ]
                | [ x1, ALWAYS INPUT, 1, 1 ]
                | [ x2, ALWAYS INPUT, 0, 0 ]
                | [ q1, ALREADY ASSIGNED, 5, 0 ]
                ---------

10  #10    Another call to fit_f to place new first output signal on fvl: q2 fit_f( PLE11R8[1] )
                fit_f: q2 placed on pin 10 of PLE11R8 fa now reflects both q1 and q2 assigned to device 1 in current solution 15         fa: q1:1 q2:1 x1:-1 x2:-1 make sure must-be-inputs can be assigned

11      assign_inputs: partial
                    --- Pnode ---
                    | lib_index: 1
     20             |     pins:      a b c d x1 x2 . . q1 q2 . . . . . . . . . . . . . .
                    | input list:    a b c d x1 q1 q2 x2
                    -------------
                  assign_inputs: inputs assigned New fvl with assignment of q2 -- no avail outputs left 25           ---fvl---
                  | [ x2, ALWAYS INPUT, 2, 1 ]
         #12      | [ x1, ALWAYS INPUT, 1, 1 ]
                  | [ q2, ALREADY ASSIGNED, 7, 1 ]
                  | [ q1, ALREADY ASSIGNED, 5, 1 ]
                  ---------

30
                q2 placed on device 1

#13    fit_f: placed q2
```

- 53 - make sure all needed signals assigned

```
assign_inputs: final
   --- Pnode ---
   | lib_index: 1
   |     pins:  a b c d x1 x2 . . q1 q2 . . . . . . . . . . . . . . .
   | input list:  a b c d x1 q1 q2 x2
   -------------
assign_inputs: inputs assigned
```

Final pNode and fvl list for device 1 as PLE11R8

```
--- Pnode ---
| lib_index: 1
|     pins:  a b c d x1 x2 . . q1 q2 . . . . . . . . . . . . . . .
| input list:  a b c d x1 q1 q2 x2
-------------
---fvl---
| [ x2, ALWAYS INPUT, 2, 1 ]
| [ x1, ALWAYS INPUT, 1, 1 ]
| [ q2, ALREADY ASSIGNED, 7, 1 ]
| [ q1, ALREADY ASSIGNED, 5, 1 ]
---------
``` still have output signals to assign (x1,x2) but cannot place them on
this device, so try a new device that will be device 2 in the current solution

14    try( 2, [ 1] )

try selects first device in lib_list that will fit x1 or x2, so try
try skips the PLE11R8 and uses P16R4

15    try_device( 2, P16R4, [ 1, 2] )

Initial pNode and fvl list for this device

```
--- Pnode ---
| lib_index: 2
|     pins:  . . . . . . . . . . . . . . . . . . . .
| input list:
-------------
---fvl---
```
16
```
| [ x2, AVAIL OUTPUT, -4, 0 ]
| [ x1, AVAIL OUTPUT, -5, 0 ]
| [ q1, ALREADY ASSIGNED, -5, 0 ]
| [ q2, ALREADY ASSIGNED, -7, 0 ]
---------
``` select first output signal (x2) and assign it to the device

```
fit_f( P16R4[2] )
```
17    fit_f: x2 placed on pin 12 of P16R4

– 54 – fa now reflects x2 assigned to device 2 in the solution list fa: q1:1 q2:1 x1:-1 x2:2 make sure must-be-inputs can be assigned assign_inputs: partial
--- Pnode ---
| lib_index: 2
|     pins:  . a d f . . . . . . . x2 . . . . . . . .
| input list: a d f q1
-------------
assign_inputs: inputs assigned

18

New fvl -- x1 is not an auxiliary output signal for x2

---fvl---
| [ x1, AVAIL OUTPUT, 1, 0 ]
| [ q1, ALREADY ASSIGNED, -1, 1 ]
| [ x2, ALREADY ASSIGNED, 4, 0 ]
| [ q2, ALREADY ASSIGNED, -1, 0 ]
---------

19 x2 placed in device fit_f: placed x2 make sure all signals can be assigned assign_inputs: final
--- Pnode ---
| lib_index: 2
|     pins:  . a d f q1 . . . . . . x2 . . . . . . . . .
| input list: a d f q1
-------------
assign_inputs: inputs assigned Updated pNode and fvl with x2 assigned to device --- Pnode ---
| lib_index: 2
|     pins:  . a d f q1 . . . . . . x2 . . . . . . . .
| input list: a d f q1
-------------
---fvl---
| [ x1, AVAIL OUTPUT, 1, 0 ]
| [ q1, ALREADY ASSIGNED, -1, 1 ]
| [ x2, ALREADY ASSIGNED, 4, 0 ]
| [ q2, ALREADY ASSIGNED, -1, 0 ]
---------

```
                             - 55 -
              Select first output signal from fvl and try to assign to device fit_f( P16R4[2] )
              fit_f: x1 placed on pin 13 of P16R4 fa reflects x1 assigned to device 2 in the current solution fa: q1:1 q2:1 x1:2 x2:2
5
                 check that must-be-inputs can be assigned

#20      assign_inputs: partial
                    --- Pnode ---
                    |  lib_index: 2
10                  |     pins:  . a d f q1 b e . . . . x2 x1 . . . . . . . .
                    |  input list:  a d f q1 b e
                    --------------
                 assign_inputs: inputs assigned New fvl with x2 assigned to device 15                  ---fvl---
                    |  [ q1, ALREADY ASSIGNED, 1, 1 ]
                    |  [ x1, ALREADY ASSIGNED, 5, 0 ]
                    |  [ x2, ALREADY ASSIGNED, 4, 0 ]
                    |  [ q2, ALREADY ASSIGNED, 1, 0 ]
                    ---------
                 fit_f: placed x1
20
        #21      final assignment -- make sure all signals can be assigned assign_inputs: final
                    --- Pnode ---
                    |  lib_index: 2
                    |     pins:  . a d f q1 b e . . . . x2 x1 . . . . . . . .
25                  |  input list:  a d f q1 b e
                    --------------
                 assign_inputs: inputs assigned Final pnode and fvl for device 2 in the current solution --- Pnode ---
30                  |  lib_index: 2
                    |     pins:  . a d f q1 b e . . . . x2 x1 . . . . . . . .
                    |  input list:  a d f q1 b e
                    --------------
                    ---fvl---
                    |  [ q1, ALREADY ASSIGNED, 1, 1 ]
                    |  [ x1, ALREADY ASSIGNED, 5, 0 ]
                    |  [ x2, ALREADY ASSIGNED, 4, 0 ]
                    |  [ q2, ALREADY ASSIGNED, 1, 0 ]
                    ---------
```

```
                                      - 56 -
                 all output signals marked already assigned in fvl so this is a solution
                 add this solution to the solution list add_soln( [ 1, 2] )

there are no solutions in the solution list yet, so this solution
                         is one of the ten best so far; add it to the list -- it will be
                         first in the list with a cost of 178 (PLE11R8) + 240 (16R4) = 418 add_soln: soln added to list try_device: exit

22       try selects the next device from the lib_list that will fit one of
                     x1 or x2, so try skips the P16R8 and selects the PLS173 try_device( 2, PLS173, [ 1, 4] )

Initial state of pnode and fvl for pls173 as the second device
                         in the current solution --- Pnode ---
                     | lib_index: 4
                     |     pins:  . . . . . . . . . . . . . . . . . . . . . . . . . .
                     | input list:
                     --------------
                     ---fvl---
                     | [ x2, AVAIL OUTPUT, -4, 0 ]
                     | [ x1, AVAIL OUTPUT, -5, 0 ]
                     | [ q1, ALREADY ASSIGNED, -5, 0 ]
                     | [ q2, ALREADY ASSIGNED, -7, 0 ]
                     --------- select first fvl output signal: x2 fit_f( PLS173[2] )
                 fit_f: x2 placed on pin 14 of PLS173
                 fa: q1:1 q2:1 x1:-1 x2:2
                     assign_inputs: partial
                         --- Pnode ---
                         | lib_index: 4
                         |     pins:  a d f . . . . . . . . . . . x2 . . . . . . . . . .
                         | input list: a d f q1
                         --------------
                     assign_inputs: inputs assigned
```

```
                                    - 57 -
                        fvl with x2 assigned ---fvl---
                        |  [ x1, AVAIL OUTPUT, 1, 0 ]
                        |  [ q1, ALREADY ASSIGNED, -1, 1 ]
                        |  [ x2, ALREADY ASSIGNED, 4, 0 ]
                        |  [ q2, ALREADY ASSIGNED, -1, 0 ]
                        ---------
 5                      fit_f: placed x2
                        assign_inputs: final
                        --- Pnode ---
                        |  lib_index: 4
                        |     pins:  a d f q1 . . . . . . . . . x2 . . . . . . . . . .
                        |  input list:  a d f q1
                        -------------
10                      assign_inputs: inputs assigned pnode and fvl with x2 assigned --- Pnode ---
                        |  lib_index: 4
15                      |     pins:  a d f q1 . . . . . . . . . x2 . . . . . . . . . .
                        |  input list:  a d f q1
                        -------------
                        ---fvl---
                        |  [ x1, AVAIL OUTPUT, 1, 0 ]
                        |  [ q1, ALREADY ASSIGNED, -1, 1 ]
                        |  [ x2, ALREADY ASSIGNED, 4, 0 ]
20                      |  [ q2, ALREADY ASSIGNED, -1, 0 ]
                        --------- select first output signal on fvl: x1 fit_f( PLS173[2] )
                        fit_f: x1 placed on pin 15 of PLS173
25                      fa: q1:1 q2:1 x1:2 x2:2
                          assign_inputs: partial
                            --- Pnode ---
                            |  lib_index: 4
                            |     pins:  a d f q1 b e . . . . . . . x2 x1 . . . . . . . . . .
                            |  input list:  a d f q1 b e
                            -------------
30                        assign_inputs: inputs assigned
                        ---fvl---
                        |  [ q1, ALREADY ASSIGNED, 1, 1 ]
                        |  [ x1, ALREADY ASSIGNED, 5, 0 ]
                        |  [ x2, ALREADY ASSIGNED, 4, 0 ]
                        |  [ q2, ALREADY ASSIGNED, 1, 0 ]
                        ---------
                        fit_f: placed x1
```

```
                        - 58 -
        assign_inputs: final
          --- Pnode ---
          | lib_index: 4
          |      pins:  a d f q1 b e . . . . . . . x2 x1 . . . . . . . . . .
          | input list:  a d f q1 b e
          -------------
        assign_inputs: inputs assigned pnode and fvl with x1 assigned --- Pnode ---
          | lib_index: 4
          |      pins:  a d f q1 b e . . . . . . . x2 x1 . . . . . . . . . .
          | input list:  a d f q1 b e
          -------------
          ---fvl---
          | [ q1, ALREADY ASSIGNED, 1, 1 ]
          | [ x1, ALREADY ASSIGNED, 5, 0 ]
          | [ x2, ALREADY ASSIGNED, 4, 0 ]
          | [ q2, ALREADY ASSIGNED, 1, 0 ]
          ---------

All fvl entries are assigned, so this is a solution add_soln( [ 1, 4] )

only one solution in list, so this is one of the ten best,
                add it to the list -- it will be second in the list with
                a cost of 178 (PLE11R8) + 522 (PLS173) = 700, which is greater
                than the cost of the solution in the list: 418 add_soln: soln added to list
        try_device: exit

At this point we have tried all four devices as the second device
                in the current solution (the two with only registers could not
                be used) so we back out and try a new first device try: exit
        try_device: exit the outermost try selects a P16R4 as a first device -- all output
            signals are marked as available try_device( 1, P16R4, [ 2] )
```

```
                                      - 59 -
                    Initial pnode and fvl for this device -- note that since this device
                        has both types of outputs, all the output signals are avail output
                        on this device --- Pnode ---
                    |  lib_index: 2
                    |      pins:  . . . . . . . . . . . . . . . . . . .
                    |  input list:
5                   -------------
                    ---fvl---
                    |  [ x2, AVAIL OUTPUT, -4, 0 ]
                    |  [ x1, AVAIL OUTPUT, -5, 0 ]
                    |  [ q1, AVAIL OUTPUT, -5, 0 ]
                    |  [ q2, AVAIL OUTPUT, -7, 0 ]
10                  --------- fit the first output signal in the fvl: x2 fit_f( P16R4[1] )
                    fit_f: x2 placed on pin 12 of P16R4

15                  show x2 assigned to device 1 in the current solution fa: q1:-1 q2:-1 x1:-1 x2:1 assign_inputs: partial
                          --- Pnode ---
                          |  lib_index: 2
20                        |      pins:  . a d f . . . . . . . x2 . . . . . . . . .
                          |  input list:  a d f q1
                          -------------
                        assign_inputs: inputs assigned
                        ---fvl---
                        |  [ q1, AVAIL OUTPUT, -1, 1 ]
                        |  [ x1, AVAIL OUTPUT, 1, 0 ]
25                      |  [ q2, AVAIL OUTPUT, -1, 0 ]
                        |  [ x2, ALREADY ASSIGNED, 4, 0 ]
                        --------- q1 is used as an input to x2, so q1 is an auxiliary output signal
                            for x2. q1 is selected for fitting at this point and placed on
                            the device
30
                        assigning q1 to pin 14
                        fit_f: aux q1 placed on pin 14 of P16R4
                        fa: q1:1 q2:-1 x1:-1 x2:1
                          assign_inputs: partial
                            --- Pnode ---
                            |  lib_index: 2
                            |      pins:  . a d f b c . . . . . x2 . q1 . . . . . .
                            |  input list:  a d f q1 b c x1
                            -------------
                          assign_inputs: inputs assigned
```

```
                                    - 60 -
         ---fvl---
         |  [ x1, AVAIL OUTPUT, 3, 1 ]
         |  [ q2, AVAIL OUTPUT, 3, 0 ]
         |  [ q1, ALREADY ASSIGNED, 5, 1 ]
         |  [ x2, ALREADY ASSIGNED, 4, 0 ]
         ---------
``` x1 is used as an input signal by q1 and is an auxiliary output signal
   for q1 -- x1 is placed on the device at this point

```
assigning x1 to pin 13
fit_f: aux x1 placed on pin 13 of P16R4
fa: q1:1 q2:-1 x1:1 x2:1
   assign_inputs: partial
      --- Pnode ---
      | lib_index: 2
      |     pins:  . a d f b c e . . . . x2 x1 q1 . . . . . .
      | input list:  a d f q1 b c x1 e
      -------------
   assign_inputs: inputs assigned
   ---fvl---
   |  [ q2, AVAIL OUTPUT, 3, 0 ]
   |  [ x1, ALREADY ASSIGNED, 5, 1 ]
   |  [ q1, ALREADY ASSIGNED, 5, 1 ]
   |  [ x2, ALREADY ASSIGNED, 4, 0 ]
   ---------
   fit_f: placed x2
```

Now the initial output signal x2 and all the auxiliaries q1 and x1
   have been placed on the device -- check that the input signals
   can be assigned and continue

```
assign_inputs: final
   --- Pnode ---
   | lib_index: 2
   |     pins:  . a d f b c e . . . . x2 x1 q1 . . . . . .
   | input list:  a d f q1 b c x1 e
   -------------
assign_inputs: inputs assigned
``` pnode and fvl reflecting assignment of x1, x2 and q1

```
   --- Pnode ---
   | lib_index: 2
   |     pins:  . a d f b c e . . . . x2 x1 q1 . . . . . .
   | input list:  a d f q1 b c x1 e
   -------------
   ---fvl---
   |  [ q2, AVAIL OUTPUT, 3, 0 ]
   |  [ x1, ALREADY ASSIGNED, 5, 1 ]
   |  [ q1, ALREADY ASSIGNED, 5, 1 ]
   |  [ x2, ALREADY ASSIGNED, 4, 0 ]
   ---------
```

```
                          - 61 -
       select the first fvl list entry: q2 and assign to the device fit_f( P16R4[1] )
       fit_f: q2 placed on pin 15 of P16R4
       fa: q1:1 q2:1 x1:1 x2:1
         assign_inputs: partial
           --- Pnode ---
           | lib_index: 2
           |     pins:  . a d f b c e . . . . x2 x1 q1 q2 . . . . .
           | input list:  a d f q1 b c x1 e q2 x2
           -------------
         assign_inputs: inputs assigned
         ---fvl---
         | [ q2, ALREADY ASSIGNED, 7, 1 ]
         | [ x1, ALREADY ASSIGNED, 5, 1 ]
         | [ q1, ALREADY ASSIGNED, 5, 1 ]
         | [ x2, ALREADY ASSIGNED, 4, 1 ]
         ---------
         fit_f: placed q2
       assign_inputs: final
         --- Pnode ---
         | lib_index: 2
         |     pins:  . a d f b c e . . . . x2 x1 q1 q2 . . . . .
         | input list:  a d f q1 b c x1 e q2 x2
         -------------
       assign_inputs: inputs assigned Final pnode and fvl for this device --- Pnode ---
       | lib_index: 2
       |     pins:  . a d f b c e . . . . x2 x1 q1 q2 . . . . .
       | input list:  a d f q1 b c x1 e q2 x2
       -------------
       ---fvl---
       | [ q2, ALREADY ASSIGNED, 7, 1 ]
       | [ x1, ALREADY ASSIGNED, 5, 1 ]
       | [ q1, ALREADY ASSIGNED, 5, 1 ]
       | [ x2, ALREADY ASSIGNED, 4, 1 ]
       --------- all the output signals have been assigned to this device -- this is a
          solution so try to add it to the solution list add_soln( [ 2] )
```

```
                                      - 62 -
             there are only two solutions in the list so this is one of the ten
                best so far -- add it to the solution list with a cost
                of 240 (P16R4) -- this is less than either of the two solutions
                in the list (418, 700) so this will be solution 1 and the others
                will sort to solution 2 (PLE11R8/P16R4) and
                solution 3 (PLE11R8/PLS173)

add_soln: soln added to list try_device: exit try selects the next device in lib_list: P16R8 try_device( 1, P16R8, [ 3] )
             --- Pnode ---
             | lib_index: 3
             |     pins: . . . . . . . . . . . . . . . . . . .
             | input list:
             -------------
             ---fvl---
             | [ q1, AVAIL OUTPUT, -5, 0 ]
             | [ q2, AVAIL OUTPUT, -7, 0 ]
             | [ x2, ALWAYS INPUT, -4, 0 ]
             | [ x1, ALWAYS INPUT, -5, 0 ]
             ---------
             fit_f( P16R8[1] )
             fit_f: q1 placed on pin 12 of P16R8
             fa: q1:1 q2:-1 x1:-1 x2:-1
                assign_inputs: partial
                   --- Pnode ---
                   | lib_index: 3
                   |     pins: . a b c d x1 . . . . . q1 . . . . . . . .
                   | input list: a b c d x1
                   -------------
                assign_inputs: inputs assigned
                ---fvl---
                | [ q2, AVAIL OUTPUT, 1, 0 ]
                | [ x1, ALWAYS INPUT, 1, 1 ]
                | [ x2, ALWAYS INPUT, 0, 0 ]
                | [ q1, ALREADY ASSIGNED, 5, 0 ]
                ---------
             fit_f: placed q1
             assign_inputs: final
                --- Pnode ---
                | lib_index: 3
                |     pins: . a b c d x1 . . . . . q1 . . . . . . . .
                | input list: a b c d x1
                -------------
             assign_inputs: inputs assigned
             --- Pnode ---
             | lib_index: 3
             |     pins: . a b c d x1 . . . . . q1 . . . . . . . .
             | input list: a b c d x1
             -------------
```

```
                    - 63 -
---fvl---
| [ q2, AVAIL OUTPUT, 1, 0 ]
| [ x1, ALWAYS INPUT, 1, 1 ]
| [ x2, ALWAYS INPUT, 0, 0 ]
| [ q1, ALREADY ASSIGNED, 5, 0 ]
---------
fit_f( P16R8[1] )
fit_f: q2 placed on pin 13 of P16R8
fa: q1:1 q2:1 x1:-1 x2:-1
  assign_inputs: partial
    --- Pnode ---
    | lib_index: 3
    |     pins:  . a b c d x1 x2 . . . . q1 q2 . . . . . . .
    | input list:  a b c d x1 q1 q2 x2
    -------------
  assign_inputs: inputs assigned
  ---fvl---
  | [ x2, ALWAYS INPUT, 2, 1 ]
  | [ x1, ALWAYS INPUT, 1, 1 ]
  | [ q2, ALREADY ASSIGNED, 7, 1 ]
  | [ q1, ALREADY ASSIGNED, 5, 1 ]
  ---------
fit_f: placed q2
assign_inputs: final
  --- Pnode ---
  | lib_index: 3
  |     pins:  . a b c d x1 x2 . . . . q1 q2 . . . . . . .
  | input list:  a b c d x1 q1 q2 x2
  -------------
assign_inputs: inputs assigned
--- Pnode ---
| lib_index: 3
|     pins:  . a b c d x1 x2 . . . . q1 q2 . . . . . . .
| input list:  a b c d x1 q1 q2 x2
-------------
---fvl---
| [ x2, ALWAYS INPUT, 2, 1 ]
| [ x1, ALWAYS INPUT, 1, 1 ]
| [ q2, ALREADY ASSIGNED, 7, 1 ]
| [ q1, ALREADY ASSIGNED, 5, 1 ]
---------
try( 2, [ 3])
  try_device( 2, P16R4, [ 3, 2] )
    --- Pnode ---
    | lib_index: 2
    |     pins:  . . . . . . . . . . . . . . . . . . .
    | input list:
    -------------
    ---fvl---
    | [ x2, AVAIL OUTPUT, -4, 0 ]
    | [ x1, AVAIL OUTPUT, -5, 0 ]
    | [ q1, ALREADY ASSIGNED, -5, 0 ]
    | [ q2, ALREADY ASSIGNED, -7, 0 ]
    ---------
```

```
                            - 64 -
fit_f( P16R4[2] )
fit_f: x2 placed on pin 12 of P16R4
fa: q1:1 q2:1 x1:-1 x2:2
  assign_inputs: partial
    --- Pnode ---
    | lib_index: 2
    |    pins:   . a d f . . . . . . . x2 . . . . . . . . .
    | input list:  a d f q1
    -------------
  assign_inputs: inputs assigned
  ---fvl---
  | [ x1, AVAIL OUTPUT, 1, 0 ]
  | [ q1, ALREADY ASSIGNED, -1, 1 ]
  | [ x2, ALREADY ASSIGNED, 4, 0 ]
  | [ q2, ALREADY ASSIGNED, -1, 0 ]
  ---------
  fit_f: placed x2
assign_inputs: final
  --- Pnode ---
  | lib_index: 2
  |    pins:   . a d f q1 . . . . . . x2 . . . . . . . . .
  | input list:  a d f q1
  -------------
assign_inputs: inputs assigned
--- Pnode ---
| lib_index: 2
|    pins:   . a d f q1 . . . . . . x2 . . . . . . . . .
| input list:  a d f q1
-------------
---fvl---
| [ x1, AVAIL OUTPUT, 1, 0 ]
| [ q1, ALREADY ASSIGNED, -1, 1 ]
| [ x2, ALREADY ASSIGNED, 4, 0 ]
| [ q2, ALREADY ASSIGNED, -1, 0 ]
---------
fit_f( P16R4[2] )
fit_f: x1 placed on pin 13 of P16R4
fa: q1:1 q2:1 x1:2 x2:2
  assign_inputs: partial
    --- Pnode ---
    | lib_index: 2
    |    pins:   . a d f q1 b e . . . . x2 x1 . . . . . . .
    | input list:  a d f q1 b e
    -------------
  assign_inputs: inputs assigned
  ---fvl---
  | [ q1, ALREADY ASSIGNED, 1, 1 ]
  | [ x1, ALREADY ASSIGNED, 5, 0 ]
  | [ x2, ALREADY ASSIGNED, 4, 0 ]
  | [ q2, ALREADY ASSIGNED, 1, 0 ]
  ---------
  fit_f: placed x1
```

```
                                     - 65 -
                            assign_inputs: final
                              --- Pnode ---
                              | lib_index: 2
                              |      pins:   . a d f q1 b e . . . . x2 x1 . . . . . . . .
                              | input list:  a d f q1 b e
                              -------------
                            assign_inputs: inputs assigned
                            --- Pnode ---
                            | lib_index: 2
                            |      pins:   . a d f q1 b e . . . . x2 x1 . . . . . . . .
                            | input list:  a d f q1 b e
                            -------------
                            ---fvl---
                            |  [ q1, ALREADY ASSIGNED, 1, 1 ]
                            |  [ x1, ALREADY ASSIGNED, 5, 0 ]
                            |  [ x2, ALREADY ASSIGNED, 4, 0 ]
                            |  [ q2, ALREADY ASSIGNED, 1, 0 ]
                            ---------
                          add_soln( [ 3, 2] )
                            add_soln: soln added to list
                          try_device: exit
                          try_device( 2, PLS173, [ 3, 4] )
                            --- Pnode ---
                            | lib_index: 4
                            |      pins:  . . . . . . . . . . . . . . . . . . . . . . . .
                            | input list:
                            -------------
                            ---fvl---
                            |  [ x2, AVAIL OUTPUT, -4, 0 ]
                            |  [ x1, AVAIL OUTPUT, -5, 0 ]
                            |  [ q1, ALREADY ASSIGNED, -5, 0 ]
                            |  [ q2, ALREADY ASSIGNED, -7, 0 ]
                            ---------
                            fit_f( PLS173[2] )
                            fit_f: x2 placed on pin 14 of PLS173
                            fa: q1:1 q2:1 x1:-1 x2:2
                              assign_inputs: partial
                                --- Pnode ---
                                | lib_index: 4
                                |      pins:  a d f . . . . . . . . . . x2 . . . . . . . . . . .
                                | input list:  a d f q1
                                -------------
                              assign_inputs: inputs assigned
                              ---fvl---
                              |  [ x1, AVAIL OUTPUT, 1, 0 ]
                              |  [ q1, ALREADY ASSIGNED, -1, 1 ]
                              |  [ x2, ALREADY ASSIGNED, 4, 0 ]
                              |  [ q2, ALREADY ASSIGNED, -1, 0 ]
                              ---------
                              fit_f: placed x2
```

```
                              - 66 -
                 assign_inputs: final
                    --- Pnode ---
                    | lib_index: 4
                    |      pins: a d f q1 . . . . . . . . . x2 . . . . . . . . . .
                    | input list: a d f q1
                    -------------
                 assign_inputs: inputs assigned
                 --- Pnode ---
 5               | lib_index: 4
                 |      pins: a d f q1 . . . . . . . . . x2 . . . . . . . . . .
                 | input list: a d f q1
                 -------------
                 ---fvl---
                 | [ x1, AVAIL OUTPUT, 1, 0 ]
10               | [ q1, ALREADY ASSIGNED, -1, 1 ]
                 | [ x2, ALREADY ASSIGNED, 4, 0 ]
                 | [ q2, ALREADY ASSIGNED, -1, 0 ]
                 ---------
                 fit_f( PLS173[2] )
                 fit_f: x1 placed on pin 15 of PLS173
                 fa: q1:1 q2:1 x1:2 x2:2
15                  assign_inputs: partial
                       --- Pnode ---
                       | lib_index: 4
                       |      pins: a d f q1 b e . . . . . . . x2 x1 . . . . . . . . . .
                       | input list: a d f q1 b e
                       -------------
                    assign_inputs: inputs assigned
20                  ---fvl---
                    | [ q1, ALREADY ASSIGNED, 1, 1 ]
                    | [ x1, ALREADY ASSIGNED, 5, 0 ]
                    | [ x2, ALREADY ASSIGNED, 4, 0 ]
                    | [ q2, ALREADY ASSIGNED, 1, 0 ]
                    ---------
                    fit_f: placed x1
25               assign_inputs: final
                    --- Pnode ---
                    | lib_index: 4
                    |      pins: a d f q1 b e . . . . . . . x2 x1 . . . . . . . . . .
                    | input list: a d f q1 b e
                    -------------
                 assign_inputs: inputs assigned
30               --- Pnode ---
                 | lib_index: 4
                 |      pins: a d f q1 b e . . . . . . . x2 x1 . . . . . . . . . .
                 | input list: a d f q1 b e
                 -------------
                 ---fvl---
                 | [ q1, ALREADY ASSIGNED, 1, 1 ]
                 | [ x1, ALREADY ASSIGNED, 5, 0 ]
                 | [ x2, ALREADY ASSIGNED, 4, 0 ]
                 | [ q2, ALREADY ASSIGNED, 1, 0 ]
                 ---------
```

- 67 -
```
         add_soln( [ 3, 4] )
           add_soln: soln added to list
         try_device: exit
       try: exit
     try_device: exit try selects the last device in the lib_list: PLS173 try_device( 1, PLS173, [ 4] )
       --- Pnode ---
       | lib_index: 4
       |    pins: . . . . . . . . . . . . . . . . . . . . . . . . .
       | input list:
       -------------
       ---fvl---
       | [ x2, AVAIL OUTPUT, -4, 0 ]
       | [ x1, AVAIL OUTPUT, -5, 0 ]
       | [ q1, ALWAYS INPUT, -5, 0 ]
       | [ q2, ALWAYS INPUT, -7, 0 ]
       ---------
       fit_f( PLS173[1] )
       fit_f: x2 placed on pin 14 of PLS173
       fa: q1:-1 q2:-1 x1:-1 x2:1
         assign_inputs: partial
           --- Pnode ---
           | lib_index: 4
           |    pins:  a d f q1 . . . . . . . . . x2 . . . . . . . . . . .
           | input list: a d f q1
           -------------
         assign_inputs: inputs assigned
         ---fvl---
         | [ x1, AVAIL OUTPUT, 1, 0 ]
         | [ q1, ALWAYS INPUT, -1, 1 ]
         | [ q2, ALWAYS INPUT, -1, 0 ]
         | [ x2, ALREADY ASSIGNED, 4, 0 ]
         ---------
         fit_f: placed x2
       assign_inputs: final
         --- Pnode ---
         | lib_index: 4
         |    pins: a d f q1 . . . . . . . . . x2 . . . . . . . . . . .
         | input list: a d f q1
         -------------
       assign_inputs: inputs assigned
       --- Pnode ---
       | lib_index: 4
       |    pins: a d f q1 . . . . . . . . . x2 . . . . . . . . . . .
       | input list: a d f q1
       -------------
```

```
                                    - 68 -
       ---fvl---
       | [ x1, AVAIL OUTPUT, 1, 0 ]
       | [ q1, ALWAYS INPUT, -1, 1 ]
       | [ q2, ALWAYS INPUT, -1, 0 ]
       | [ x2, ALREADY ASSIGNED, 4, 0 ]
       ---------
       fit_f( PLS173[1] )
       fit_f: x1 placed on pin 15 of PLS173
       fa: q1:-1 q2:-1 x1:1 x2:1
         assign_inputs: partial
           --- Pnode ---
           | lib_index: 4
           |     pins:  a d f q1 b e . . . . . . . x2 x1 . . . . . . . . . .
           | input list:  a d f q1 b e
           -------------
         assign_inputs: inputs assigned
         ---fvl---
         | [ q1, ALWAYS INPUT, 1, 1 ]
         | [ q2, ALWAYS INPUT, 1, 0 ]
         | [ x1, ALREADY ASSIGNED, 5, 0 ]
         | [ x2, ALREADY ASSIGNED, 4, 0 ]
         ---------
       fit_f: placed x1
       assign_inputs: final
         --- Pnode ---
         | lib_index: 4
         |     pins:  a d f q1 b e . . . . . . . x2 x1 . . . . . . . . . .
         | input list:  a d f q1 b e
         -------------
       assign_inputs: inputs assigned
       --- Pnode ---
       | lib_index: 4
       |     pins:  a d f q1 b e . . . . . . . x2 x1 . . . . . . . . . .
       | input list:  a d f q1 b e
       -------------
       ---fvl---
       | [ q1, ALWAYS INPUT, 1, 1 ]
       | [ q2, ALWAYS INPUT, 1, 0 ]
       | [ x1, ALREADY ASSIGNED, 5, 0 ]
       | [ x2, ALREADY ASSIGNED, 4, 0 ]
       ---------
       try( 2, [ 4])
         try_device( 2, PLE11RB, [ 4, 1] )
           --- Pnode ---
           | lib_index: 1
           |     pins:  . . . . . . . . . . . . . . . . . . . . . . . .
           | input list:
           -------------
           ---fvl---
           | [ q1, AVAIL OUTPUT, -5, 0 ]
           | [ q2, AVAIL OUTPUT, -7, 0 ]
           | [ x2, ALREADY ASSIGNED, -4, 0 ]
           | [ x1, ALREADY ASSIGNED, -5, 0 ]
           ---------
```

```
                                  - 69 -
fit_f( PLE11R8[4] )
fit_f: q1 placed on pin 9 of PLE11R8
fa: q1:2 q2:-1 x1:1 x2:1
   assign_inputs: partial
      --- Pnode ---
      | lib_index: 1
      |     pins:  a b c d . . . . q1 . . . . . . . . . . . . . . .
      | input list:  a b c d x1
      -------------
   assign_inputs: inputs assigned
   ---fvl---
   | [ q2, AVAIL OUTPUT, 1, 0 ]
   | [ x1, ALREADY ASSIGNED, 1, 1 ]
   | [ q1, ALREADY ASSIGNED, 5, 0 ]
   | [ x2, ALREADY ASSIGNED, 0, 0 ]
   ---------
   fit_f: placed q1
assign_inputs: final
   --- Pnode ---
   | lib_index: 1
   |     pins:  a b c d x1 . . . q1 . . . . . . . . . . . . . . .
   | input list:  a b c d x1
   -------------
assign_inputs: inputs assigned
--- Pnode ---
| lib_index: 1
|     pins:  a b c d x1 . . . q1 . . . . . . . . . . . . . . .
| input list:  a b c d x1
-------------
---fvl---
| [ q2, AVAIL OUTPUT, 1, 0 ]
| [ x1, ALREADY ASSIGNED, 1, 1 ]
| [ q1, ALREADY ASSIGNED, 5, 0 ]
| [ x2, ALREADY ASSIGNED, 0, 0 ]
---------
fit_f( PLE11R8[2] )
fit_f: q2 placed on pin 10 of PLE11R8
fa: q1:2 q2:2 x1:1 x2:1
   assign_inputs: partial
      --- Pnode ---
      | lib_index: 1
      |     pins:  a b c d x1 . . . q1 q2 . . . . . . . . . . . . . . .
      | input list:  a b c d x1 q1 q2 x2
      -------------
   assign_inputs: inputs assigned
   ---fvl---
   | [ q2, ALREADY ASSIGNED, 7, 1 ]
   | [ q1, ALREADY ASSIGNED, 5, 1 ]
   | [ x2, ALREADY ASSIGNED, 2, 1 ]
   | [ x1, ALREADY ASSIGNED, 1, 1 ]
   ---------
   fit_f: placed q2
```

```
                            - 70 -
             assign_inputs: final
                --- Pnode ---
                | lib_index: 1
                |     pins:  a b c d x1 x2 . . q1 q2 . . . . . . . . . . . . . .
                | input list:  a b c d x1 q1 q2 x2
                -------------
             assign_inputs: inputs assigned
                --- Pnode ---
                | lib_index: 1
                |     pins:  a b c d x1 x2 . . q1 q2 . . . . . . . . . . . . . .
                | input list:  a b c d x1 q1 q2 x2
                -------------
             ---fvl---
                | [ q2, ALREADY ASSIGNED, 7, 1 ]
                | [ q1, ALREADY ASSIGNED, 5, 1 ]
                | [ x2, ALREADY ASSIGNED, 2, 1 ]
                | [ x1, ALREADY ASSIGNED, 1, 1 ]
                ---------
             add_soln( [ 4, 1] )
                add_soln: soln added to list
             try_device: exit
             try_device( 2, P16R4, [ 4, 2] )
                --- Pnode ---
                | lib_index: 2
                |     pins:  . . . . . . . . . . . . . . . . . . .
                | input list:
                -------------
             ---fvl---
                | [ q1, AVAIL OUTPUT, -5, 0 ]
                | [ q2, AVAIL OUTPUT, -7, 0 ]
                | [ x2, ALREADY ASSIGNED, -4, 0 ]
                | [ x1, ALREADY ASSIGNED, -5, 0 ]
                ---------
             fit_f( P16R4[2] )
             fit_f: q1 placed on pin 14 of P16R4
             fa: q1:2 q2:-1 x1:1 x2:1
                assign_inputs: partial
                   --- Pnode ---
                   | lib_index: 2
                   |     pins:  . a b c d . . . . . . . . q1 . . . . . .
                   | input list:  a b c d x1
                   -------------
                assign_inputs: inputs assigned
                ---fvl---
                   | [ q2, AVAIL OUTPUT, 1, 0 ]
                   | [ x1, ALREADY ASSIGNED, 1, 1 ]
                   | [ q1, ALREADY ASSIGNED, 5, 0 ]
                   | [ x2, ALREADY ASSIGNED, 0, 0 ]
                   ---------
                fit_f: placed q1
```

```
                            - 71 -
                assign_inputs: final
                  --- Pnode ---
                  | lib_index: 2
                  |     pins:  . a b c d x1 . . . . . . . q1 . . . . . . .
                  | input list:  a b c d x1
                  ------------- assign_inputs: inputs assigned
                --- Pnode ---
                | lib_index: 2
                |     pins:  . a b c d x1 . . . . . . . q1 . . . . . . .
                | input list:  a b c d x1
                -------------
                ---fvl---
                | [ q2, AVAIL OUTPUT, 1, 0 ]
                | [ x1, ALREADY ASSIGNED, 1, 1 ]
                | [ q1, ALREADY ASSIGNED, 5, 0 ]
                | [ x2, ALREADY ASSIGNED, 0, 0 ]
                ---------
                fit_f( P16R4[2] )
                fit_f: q2 placed on pin 15 of P16R4
                fa: q1:2 q2:2 x1:1 x2:1
                  assign_inputs: partial
                    --- Pnode ---
                    | lib_index: 2
                    |     pins:  . a b c d x1 . . . . . . . q1 q2 . . . . .
                    | input list:  a b c d x1 q1 q2 x2
                    -------------
                  assign_inputs: inputs assigned
                  ---fvl---
                  | [ q2, ALREADY ASSIGNED, 7, 1 ]
                  | [ q1, ALREADY ASSIGNED, 5, 1 ]
                  | [ x2, ALREADY ASSIGNED, 2, 1 ]
                  | [ x1, ALREADY ASSIGNED, 1, 1 ]
                  ---------
                fit_f: placed q2
                assign_inputs: final
                  --- Pnode ---
                  | lib_index: 2
                  |     pins:  . a b c d x1 x2 . . . . . . q1 q2 . . . . .
                  | input list:  a b c d x1 q1 q2 x2
                  -------------
                assign_inputs: inputs assigned
                --- Pnode ---
                | lib_index: 2
                |     pins:  . a b c d x1 x2 . . . . . . q1 q2 . . . . .
                | input list:  a b c d x1 q1 q2 x2
                -------------
                ---fvl---
                | [ q2, ALREADY ASSIGNED, 7, 1 ]
                | [ q1, ALREADY ASSIGNED, 5, 1 ]
                | [ x2, ALREADY ASSIGNED, 2, 1 ]
                | [ x1, ALREADY ASSIGNED, 1, 1 ]
                ---------
```

```
                        - 72 -
        add_soln( [ 4, 2] )
          add_soln: soln added to list
        try_device: exit
        try_device( 2, P16R8, [ 4, 3] )
          --- Pnode ---
          | lib_index: 3
          |     pins: . . . . . . . . . . . . . . . . . . .
          | input list:
          -------------
          ---fvl---
          | [ q1, AVAIL OUTPUT, -5, 0 ]
          | [ q2, AVAIL OUTPUT, -7, 0 ]
          | [ x2, ALREADY ASSIGNED, -4, 0 ]
          | [ x1, ALREADY ASSIGNED, -5, 0 ]
          ---------
        fit_f( P16R8[2] )
        fit_f: q1 placed on pin 12 of P16R8
        fa: q1:2 q2:-1 x1:1 x2:1
          assign_inputs: partial
            --- Pnode ---
            | lib_index: 3
            |     pins: . a b c d . . . . . . q1 . . . . . . . .
            | input list: a b c d x1
            -------------
          assign_inputs: inputs assigned
          ---fvl---
          | [ q2, AVAIL OUTPUT, 1, 0 ]
          | [ x1, ALREADY ASSIGNED, 1, 1 ]
          | [ q1, ALREADY ASSIGNED, 5, 0 ]
          | [ x2, ALREADY ASSIGNED, 0, 0 ]
          ---------
          fit_f: placed q1
        assign_inputs: final
          --- Pnode ---
          | lib_index: 3
          |     pins: . a b c d x1 . . . . . q1 . . . . . . . .
          | input list: a b c d x1
          -------------
        assign_inputs: inputs assigned
        --- Pnode ---
        | lib_index: 3
        |     pins: . a b c d x1 . . . . . q1 . . . . . . . .
        | input list: a b c d x1
        -------------
        ---fvl---
        | [ q2, AVAIL OUTPUT, 1, 0 ]
        | [ x1, ALREADY ASSIGNED, 1, 1 ]
        | [ q1, ALREADY ASSIGNED, 5, 0 ]
        | [ x2, ALREADY ASSIGNED, 0, 0 ]
        ---------
        fit_f( P16R8[2] )
        fit_f: q2 placed on pin 13 of P16R8
        fa: q1:2 q2:2 x1:1 x2:1
```

```
                            - 73 -
            assign_inputs: partial
               --- Pnode ---
               | lib_index: 3
               |      pins:  . a b c d x1 . . . . . q1 q2 . . . . . . .
               | input list: a b c d x1 q1 q2 x2
               -------------
            assign_inputs: inputs assigned
               ---fvl---
               | [ q2, ALREADY ASSIGNED, 7, 1 ]
               | [ q1, ALREADY ASSIGNED, 5, 1 ]
               | [ x2, ALREADY ASSIGNED, 2, 1 ]
               | [ x1, ALREADY ASSIGNED, 1, 1 ]
               ---------
            fit_f: placed q2
            assign_inputs: final
               --- Pnode ---
               | lib_index: 3
               |      pins:  . a b c d x1 x2 . . . . q1 q2 . . . . . . .
               | input list: a b c d x1 q1 q2 x2
               -------------
            assign_inputs: inputs assigned
               --- Pnode ---
               | lib_index: 3
               |      pins:  . a b c d x1 x2 . . . . q1 q2 . . . . . . .
               | input list: a b c d x1 q1 q2 x2
               -------------
               ---fvl---
               | [ q2, ALREADY ASSIGNED, 7, 1 ]
               | [ q1, ALREADY ASSIGNED, 5, 1 ]
               | [ x2, ALREADY ASSIGNED, 2, 1 ]
               | [ x1, ALREADY ASSIGNED, 1, 1 ]
               ---------
            add_soln( [ 4, 3] )
               add_soln: soln added to list
            try_device: exit
          try: exit
        try_device: exit all devices have been used as the first device, so all solutions
         have been generated at this point -- exit try and output
         the solution list try: exit
```

- 74 -

23 --- Solution list --- solution 1  cost 240
    device list: P16R4
    eqn assignments: q1:P16R4[1] q2:P16R4[1] x1:P16R4[1] x2:P16R4[1]

solution 2  cost 418
    device list: PLE11R8 P16R4
    eqn assignments: q1:PLE11R8[1] q2:PLE11R8[1] x1:P16R4[2] x2:P16R4[2]

solution 3  cost 480
    device list: P16R8 P16R4
    eqn assignments: q1:P16R8[1] q2:P16R8[1] x1:P16R4[2] x2:P16R4[2]

solution 4  cost 700
    device list: PLE11R8 PLS173
    eqn assignments: q1:PLE11R8[1] q2:PLE11R8[1] x1:PLS173[2] x2:PLS173[2]

solution 5  cost 700
    device list: PLS173 PLE11R8
    eqn assignments: q1:PLE11R8[2] q2:PLE11R8[2] x1:PLS173[1] x2:PLS173[1]

solution 6  cost 762
    device list: P16R8 PLS173
    eqn assignments: q1:P16R8[1] q2:P16R8[1] x1:PLS173[2] x2:PLS173[2]

solution 7  cost 762
    device list: PLS173 P16R4
    eqn assignments: q1:P16R4[2] q2:P16R4[2] x1:PLS173[1] x2:PLS173[1]

solution 8  cost 762
    device list: PLS173 P16R8
    eqn assignments: q1:P16R8[2] q2:P16R8[2] x1:PLS173[1] x2:PLS173[1]

We claim:

1. A method of displaying capillary electrophoretograms, the method including:
   (a) electrophoresing a biological fluid in a capillary, the fluid comprising a plurality of biological constituents;
   (b) passing a light beam through the fluid at a predetermined position into the capillary;
   (c) detecting with respect to time a plurality of quantitative absorbance values related to the absorbance of the light beam by the biological constituents of the fluid in the capillary;
   (d) retaining the detected absorbance values in a memory device;
   (e) selecting a range of color characteristic values;
   (f) selecting a range of absorbance values;
   (g) correlating the range of color characteristic values to the range of absorbance values;
   (h) relating each of the retained absorbance values to the range of absorbance values;
   (i) selecting a color characteristic value from the range of color characteristic values for each retained absorbance value; and
   (j) displaying the selected color characteristic values as a stripe pattern including a plurality of stripes, the stripe pattern having an axis related to time and the stripes being spaced from each other on the axis, the color characteristic values of the stripes correlating to the retained absorbance values with respect to time, wherein (i) the stripes qualitatively represent the concentration of the biological constituents in the fluid, and (ii) different stripes have the same or have different color characteristic values.

2. A method as in claim 1 wherein displaying the color characteristic values includes displaying the values on a computer display screen.

3. A method as in claim 1 wherein displaying the color characteristic values includes printing the values.

4. A method as in claim 1 wherein the range of color characteristic values is a range of varying color.

5. The method of claim 1 wherein the step of displaying comprises:
   (a) displaying on a display the absorbance values as a graph having absorbance value on a vertical axis and time on a horizontal axis; and
   (b) displaying the stripe pattern on the same display, the stripe pattern having a horizontal axis related to time, wherein there is a one-to-one correspondence between absorbance values displayed in the graph and absorbance values displayed in the stripe pattern.

6. A method as in claim 1 wherein the range of color characteristic values comprises a range of hues or shades of gray.

7. A method as in claim 1 wherein the stripes of the stripe pattern have the same height on the axis.

8. A method as in claim 1 wherein the stripes of the stripe pattern each have multiple color characteristic values.

9. A method of displaying capillary electrophoresis electrophoretograms, the method including:
   (a) concurrently performing electrophoresis of biological fluids in a plurality of capillaries, each of the biological fluids comprising a plurality of biological constituents;
   (b) passing a light beam through the fluid at a predetermined position into each capillary;
   (c) detecting with respect to time a plurality of quantitative absorbance values related to the absorbance of the light beam by the biological constituents of the fluid in each of the capillaries;
   (d) retaining the detected absorbance values for each capillary in a memory device;
   (e) selecting a range of color characteristic values for each capillary;
   (f) selecting a range of absorbance values for each capillary;
   (g) correlating the range of color characteristic values to the range of absorbance values for each capillary;
   (h) relating each of the retained absorbance values to the range of absorbance values for each capillary;
   (i) selecting a color characteristic value from the range of color characteristic values for each retained absorbance value for each capillary; and
   (j) displaying the selected color characteristic values for each of the capillaries as a stripe pattern including a plurality of stripes, each stripe pattern having an axis related to time and the stripes being spaced from each other on the axis, the color characteristic values of the stripes correlating to the retained absorbance values with respect to time, wherein (i) the stripes qualitatively represent the concentration of the biological constituents in the fluid, and (ii) different stripes have the same or have different color characteristic values.

10. A method as in claim 9 wherein displaying the color characteristic values includes displaying the values on a computer display screen.

11. A method as in claim 9 wherein displaying the color characteristic values includes printing the values.

12. A method as in claim 9 wherein the stripes are aligned horizontally with respect to time.

13. A method as in claim 9 wherein the range of color characteristic values is monochromatic.

14. The method of claim 9 wherein the step of displaying comprises:
   (a) displaying on a display the retained absorbance values for a capillary as a graph having absorbance value on a vertical axis and time on a horizontal axis; and
   (b) displaying the stripe pattern on the same display, the stripe pattern having a horizontal axis related to time, wherein there is a one-to-one correspondence between absorbance values displayed in the graph and absorbance values displayed in the stripe pattern.

15. A method as in claim 9 wherein the stripes of the stripe pattern have the same height on the axis.

16. A method as in claim 9 wherein the stripes of the stripe pattern each have multiple color characteristic values.

17. A method for displaying capillary electrophoresis measurements, the method including:
   (a) electrophoresing a biological liquid in a capillary, the liquid comprising a plurality of biological constituents;
   (b) passing a light beam through the liquid at a predetermined position into the capillary;
   (c) detecting with respect to time the quantitative absorbance of the light beam by the biological constituents of the liquid during at least a portion of the electrophoresising time;
   (d) retaining the detected absorbance in a memory device;
   (e) selecting a range of color characteristic values;
   (f) selecting a range of absorbance values;
   (g) correlating the range of color characteristic values to the range of absorbance values;
   (h) relating the retained absorbance detected at predetermined times to the range of absorbance values;

(i) selecting a color characteristic value from the range of color characteristic values for each predetermined time; and (j) displaying the selected color characteristic values as a stripe pattern including a plurality of stripes, the stripe pattern having an axis related to time and the stripes being spaced from each other on the axis, the color characteristic values of the stripes correlating to the retained absorbance with respect to time, wherein (i) the stripes qualitatively represent the concentration of the biological constituents in the fluid, and (ii) different stripes have the same or have different color characteristic values.

18. A method as in claim 17 wherein the step of displaying includes displaying the selected color characteristic values as electrophoresising occurs.

19. A method as in claim 17 wherein step (h) comprises determining a ratio according to the value of the absorbance within the range of absorbance values, and step (i) comprises selecting the color characteristic value according to the ratio.

20. A method as in claim 19 wherein the range of absorbance values has an upper limit and a lower limit.

21. A method as in claim 20 wherein the method includes varying the upper limit.

22. A method as in claim 19 wherein the method includes selecting maximum and minimum absorbance values from the absorbance values detected and setting the range of absorbance values to the maximum and minimum values.

23. A method as in claim 17 wherein the selected color characteristic values are displayed with respect to electrophoresising time.

24. A method as in claim 23 wherein the method includes displaying the detected absorbance as a graph having absorbance value on a vertical axis and time on a horizontal axis.

25. A method as in claim 24 wherein the selected color characteristic values time axis and the graph time axis are horizontally aligned.

26. A method as in claim 25 wherein the stripe pattern axis corresponds to electrophoresing time.

27. A method as in claim 26 wherein the graph is displayed on the stripe pattern.

28. A method as in claim 26 wherein there is a one-to-one correspondence between absorbance values displayed in the graph and absorbance values displayed in the stripe pattern.

29. A method as in claim 17 wherein the range of color characteristic values is nonlinear.

30. A method as in claim 17 wherein the range of color characteristic values is linear.

31. A method as in claim 17 wherein the range of color characteristic values is visually differing from one end of the range to the other end of the range.

32. A method as in claim 17 wherein the stripes of the stripe pattern have the same height on the axis.

33. A method as in claim 17 wherein the stripes of the stripe pattern each have multiple color characteristic values.

34. A capillary electrophoresis apparatus, the apparatus comprising:

(a) means for electrophoresing a biological fluid in a capillary, the fluid comprising a plurality of biological constituents;

(b) means for passing a light beam through the fluid at a predetermined position into the capillary;

(c) means for detecting with respect to time a plurality of quantitative absorbance values related to the absorbance of the light beam by the biological constituents of the fluid in the capillary;

(d) means for retaining the detected absorbance values;

(e) means for selecting at least one range of color characteristic values;

(f) means for selecting a range of absorbance values;

(g) means for correlating the range of color characteristic values to the range of absorbance values;

(h) means for relating each of the retained absorbance values to the range of absorbance values;

(i) means for selecting a color characteristic value from the range of color characteristic values for each retained absorbance value; and (j) means for displaying the selected color characteristic values as a stripe pattern including a plurality of stripes, the stripe pattern having an axis related to time and the stripes being spaced from each other on the axis, the color characteristic values of the stripes correlating to the retained absorbance values with respect to time, wherein (i) the stripes qualitatively represent the concentration of the biological constituents in the fluid, and (ii) different stripes have the same or have different color characteristic values.

35. An apparatus as in claim 34 wherein the displaying means includes means for displaying the values on a computer display screen.

36. An apparatus as in claim 34 wherein the means for displaying the color characteristic values includes means for printing the values.

37. An apparatus as in claim 34 wherein the range of color characteristic values is a range of varying color.

38. The apparatus of claim 34 wherein the means for displaying comprises:

(a) means for displaying on a display the retained absorbance values as a graph having absorbance value on a vertical axis and time on a horizontal axis; and (b) means for displaying the stripe pattern on the same display, the stripe pattern having a horizontal axis related to time, wherein there is a one-to-one correspondence between absorbance values displayed in the graph and absorbance values displayed in the stripe pattern.

39. An apparatus as in claim 34 wherein the stripes of the stripe pattern have the same height on the axis.

40. An apparatus as in claim 34 wherein the stripes of the stripe pattern each have multiple color characteristic values.

41. An electrophoresis apparatus, the apparatus comprising:

(a) means for concurrently performing electrophoresis of biological fluids in a plurality of capillaries, the fluids comprising a plurality of biological constituents;

(b) means for passing a light beam through the fluid at a predetermined position into each capillary;

(c) means for detecting with respect to time a plurality of quantitative absorbance values related to the absorbance of the light beam by the biological constituents of the fluid in each of the capillaries;

(d) means for retaining the detected absorbance values;

(e) means for selecting at least one range of color characteristic values for each capillary;

(f) means for selecting a range of absorbance values for each capillary;

(g) means for correlating the range of color characteristic values to the range of absorbance values for each capillary;

(h) means for relating each of the retained absorbance values to the range of absorbance values for each capillary;

(i) means for selecting a color characteristic value from the range of color characteristic values for each retained absorbance value for each capillary; and (j) means for displaying the selected color characteristic values for each of the capillaries as a stripe pattern including a plurality of stripes, each stripe pattern having an axis related to time and the stripes being spaced from each other on the axis, the color characteristic values of the stripes correlating to the retained absorbance values with respect to time, wherein (i) the stripes qualitatively represent the concentration of the biological constituents in the fluid, and (ii) different stripes have the same or have different color characteristic values.

42. An apparatus as in claim 41 wherein the means for displaying the color characteristic values includes means for displaying the values on a computer display screen.

43. An apparatus as in claim 41 wherein the means for displaying the color characteristic values includes means for printing the values.

44. An apparatus as in claim 41 wherein the stripes are aligned horizontally with respect to time.

45. An apparatus as in claim 41 wherein the range of color characteristic values is monochromatic.

46. The apparatus of claim 41 wherein the means for displaying comprises:

(a) means for displaying on a display the retained absorbance values for a capillary as a graph having absorbance value on a vertical axis and time on a horizontal axis; and (b) means for displaying the stripe pattern on the same display, the stripe pattern having a horizontal axis related to time, wherein there is a one-to-one correspondence between absorbance values displayed in the graph and absorbance values displayed in the stripe pattern.

47. An electrophoresis apparatus, the apparatus including:

(a) means for electrophoresing a biological liquid in a capillary, the liquid comprising a plurality of biological constituents;

(b) means for passing a light beam through the liquid at a predetermined position into the capillary;

(c) means for detecting with respect to time the quantitative absorbance of the light beam by the biological constituents of the liquid during at least a portion of the electrophoresising time;

(d) means for retaining the detected absorbance;

(e) means for selecting at least one range of color characteristic values;

(f) means for selecting a range of absorbance values;

(g) means for correlating the range of color characteristic values to the range of absorbance values;

(h) means for relating the retained absorbance values detected at predetermined times to the range of absorbance values;

(i) means for selecting a color characteristic value from the range of color characteristic values for each predetermined time; and (j) means for displaying the selected color characteristic values as a stripe pattern including a plurality of stripes, the stripe pattern having an axis related to time and the stripes being spaced from each other on the axis, the color characteristic values of the stripes correlating to the retained absorbance with respect to time, wherein (i) the stripes qualitatively represent the concentration of the biological constituents in the fluid, and (ii) different stripes have the same or have different color characteristic values.

48. An apparatus as in claim 47 wherein the means for relating includes means for determining a ratio according to the value of the absorbance within the range of absorbance values, and the means for selecting includes means for selecting the color characteristic value according to the ratio.

49. An apparatus as in claim 48 wherein the means for selecting a range of absorbance values includes means for setting an upper limit and a lower limit for the absorbance values.

50. An apparatus as in claim 49 wherein the means for selecting a range of absorbance values includes means for varying the upper limit.

51. An apparatus as in claim 49 wherein the means for setting the upper and lower limit includes means for selecting maximum and minimum absorbance values from the absorbance values detected and setting the range of absorbance values to the maximum and minimum values.

52. An apparatus as in claim 47 including means for displaying the selected color characteristic values with respect to electrophoresising time.

53. An apparatus as in claim 52 including means for displaying the detected absorbance as a graph having absorbance value on a vertical axis and time on a horizontal axis.

54. An apparatus as in claim 53 wherein the selected color characteristic values time axis and the graph time axis are horizontally aligned.

55. An apparatus as in claim 54 wherein the stripe pattern has a length which corresponds to electrophoresising time.

56. An apparatus as in claim 55 wherein the graph is displayed on the stripe pattern.

57. An apparatus as in claim 52 wherein there is a one-to-one correspondence between absorbance values displayed in the graph and absorbance values displayed in the stripe pattern.

58. An apparatus as in claim 47 wherein the range of color characteristic values is monochromatic.

59. An apparatus as in claim 47 wherein the range of color characteristic values is visually differing from one end of the range to the other end of the range.

60. The apparatus of claim 47 wherein the means for displaying comprises:

(a) means for displaying on a display the retained absorbance as a graph having absorbance value on a vertical axis and time on a horizontal axis; and (b) means for displaying on the same display, the stripe pattern having a horizontal axis related to time, wherein there is a one-to-one correspondence between absorbance values displayed in the graph and absorbance values displayed in the strip pattern.

61. An apparatus as in claim 47 wherein the stripes of the stripe pattern have the same height on the axis.

62. An apparatus as in claim 47 wherein the stripes of the stripe pattern each have multiple color characteristic values.

63. An electrophoresis apparatus for use with reagent segments wherein the reagent segments have a plurality of wells, the apparatus comprising:

(a) a plurality of capillaries, each capillary having a first end and a second end;

(b) means for simultaneously positioning a first end of each of the capillaries into selected distinct ones of the reagent segment wells;

(c) a manifold defining a common conduit including means for receiving the second end of each of the capillaries into the common conduit and thereby establishing a common liquid path between the second ends of the capillaries;

(d) an electrode in the manifold;

(e) means for passing a light beam through a biological liquid at a predetermined position into each capillary, the liquid comprising a plurality of biological constituents;

(f) means for detecting with respect to time the quantitative absorbance of the light beam by the biological constituents of the liquid in each capillary during at least a portion of the electrophoresising time;

(g) means for retaining the detected absorbance;

(h) means for selecting at least one range of color characteristic values for each capillary;

(i) means for selecting a range of absorbance values for each capillary, (j) means for correlating the range of color characteristic values to the range of absorbance values for each capillary;

(k) means for relating each of the retained absorbance values detected at predetermined times to the range of absorbance values for each capillary;

(l) means for selecting a color characteristic value from the range of color characteristic values for each capillary for each predetermined time; and (m) means for displaying the selected color characteristic values for each of the capillaries as a stripe pattern including a plurality of stripes, each stripe pattern having an axis related to time and the stripes being spaced from each other on the axis, the color characteristic values of the stripes correlating to the retained absorbance values with respect to time, wherein (i) the stripes qualitatively represent the concentration of the biological constituents in the fluid, and (ii) different stripes have the same or have different color characteristic values.

64. An apparatus as in claim 63 wherein the means for relating includes means for determining a ratio according to the value of the absorbance within the range of absorbance values, and the means for selecting includes means for selecting the color characteristic value according to the ratio.

65. An apparatus as in claim 63 including means for displaying the selected color characteristic values with respect to electrophoresising time.

66. An apparatus as in claim 63 wherein the range of color characteristic values is monochromatic.

67. An apparatus as in claim 63 wherein the stripes of the stripe pattern have the same height on the axis.

68. An apparatus as in claim 63 wherein the stripes of the stripe pattern each have multiple color characteristic values.

69. A method of displaying capillary electrophoresis electrophoretograms including:

(a) electrophoresing a biological fluid in a capillary, the fluid comprising a plurality of biological constituents;

(b) passing a light beam through the fluid at a predetermined position into the capillary;

(c) detecting with respect to time a plurality of quantitative values related to absorbance characteristics of the biological constituents of the fluid in the capillary;

(d) retaining the detected values in a memory device;

(e) selecting a range of color characteristic values;

(f) selecting a range of absorbance values;

(g) correlating the range of color characteristic values to the range of absorbance values;

(h) relating each of the retained quantitative values to the range of absorbance values;

(i) selecting a color characteristic value from the range of color characteristic values for each detected value; and (j) displaying the selected color characteristic values as a stripe pattern including a plurality of stripes, the stripe pattern having an axis related to time and the stripes being spaced from each other on the axis, the color characteristic values of the stripes correlating to the retained values with respect to time, wherein (i) the stripes qualitatively represent the concentration of the biological constituents in the fluid, and (ii) different stripes have the same or have different color characteristic values.

70. A method as in claim 69 wherein displaying the color characteristic values includes displaying the values on a computer display screen.

71. A method as in claim 69 wherein displaying the color characteristic values includes printing the values.

72. A method as in claim 69 wherein the stripes of the stripe pattern have the same height on the axis.

73. A method as in claim 69 wherein the stripes of the stripe pattern each have multiple color characteristic values.

* * * * *